United States Patent
Bell et al.

[11] Patent Number: 6,166,072
[45] Date of Patent: Dec. 26, 2000

[54] AMINO ACID DERIVATIVES

[75] Inventors: Stanley Charles Bell, Narberth, Pa.; Michael De Vivo, New York, N.Y.; Allen Hopper, Somerset, N.J.; Methvin Isaac; Anne O'Brien, both of Ontario, Canada; Vassil Ilya Ognyanov, Princeton, N.J.; Richard Schumacher, Monmouth Junction, N.J.

[73] Assignee: Allelix Neuroscience, Inc., Canada

[21] Appl. No.: 09/342,492

[22] Filed: Jun. 29, 1999

Related U.S. Application Data

[63] Continuation-in-part of application No. 09/128,027, Aug. 3, 1998.

[51] Int. Cl.$^7$ .................................................. A61K 31/21
[52] U.S. Cl. .......................... 514/510; 514/539; 514/562; 560/10; 560/12; 560/16; 562/420; 562/427; 562/429
[58] Field of Search ................................ 560/10, 16, 12; 562/426, 427, 429; 514/510, 539, 562

[56] References Cited

U.S. PATENT DOCUMENTS 3,624,143  11/1971  Shen et al. ........................... 260/516

FOREIGN PATENT DOCUMENTS 0 326 326 B1  8/1989  European Pat. Off. .

OTHER PUBLICATIONS

Chem Abstracts Online Printout 1976:90549, rn=5191–80–0;5575–08–6(month unavailable), 1975.
Angelo Fontana, Selective Removal of Sulphur Protecting Groups of Cysteine Residues by Sulphenyl Halides, J.C.S. Chem. Comm, pp. 976–977 (1975).
Zee–Cheng and Cheng, "Experimental Antileukemic Agents. Preparation and Structure–Activity Study of S–Tritylcysteine and Related Compounds", *J. Med. Chem.*, 13:414–418, 1970.
Zee–Cheng and Cheng, "Structural Modification of S–Trityl–L–cysteine. Preparation of Some S–(Substituted Trityl)–L–cysteines and Dipeptides of S–Trityl–L–cysteine", *J. Med. Chem.*, 15:13–16, 1972.
Dhar et al., "Design, Synthesis and Evaluation of Substituted Triarylnipecotic Acid Derivatives as GABA Uptake Inhibitors: Identification of a Ligand with Moderate Affinity and Selectivity for the Cloned Human GABA Transporter GAT–3", *J. Med. Chem.*, 37:2334–2342, 1994.
Photaki et al., "On Cysteine and Cystine Peptides. Part V. S–Trityl–and S–Diphenyl–methyl–cysteine and –cysteine Peptides", *J. Chem. Soc. (C)*, 2683–2687, 1970.
Pless, "Properties and suitability of the 10, 11–dihydro–5 H–dibenzo[a, d]cyclohepten–5–yl–group (=5–dibenzosuberyl group) as a new protecting group for amines, amino–acids, alcohols, thiols andcarboxylic acids", *Helvetica Chemica Acta*, 59:499–512, 1976.
Zervas and Photaki, "On Cystein and Cystine Peptides. I. New S–Protecting Groups for Cysteine", *J. Am. Chem. Soc.*, 84: 3887–3897, 1962.

*Primary Examiner*—Samuel Barts
*Attorney, Agent, or Firm*—Dechert

[57] ABSTRACT

Described herein are compounds having the general formula:

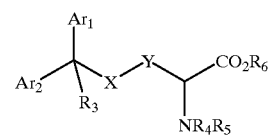

wherein:
$Ar^1$ and $Ar^2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NRR'$, NRR', $CO_2R$ (where R and R' are independently selected from the group consisting of H and alkyl) and a second aryl group, which may be substituted as above;
wherein any cycloalkyl or aryl substituent is linked to $Ar^1$ or $Ar^2$ by a bridging element which may be a single bond, a vinylene group, an ethynylene group, a Z group, a —Z—$(CH_2)_n$— group, a —$(CH_2)_n$—Z— group, or a —Z—$(CH_2)_n$—Z— group, where Z represents an O atom, a S atom, an NH group or an N-alkyl group, and n is an integer from 1 to 4;
wherein $Ar^1$ and $Ar^2$ may be attached to the central atom to which they are connected by a single bond, an alkylene, alkenylene or alkynylene group;
wherein $Ar^1$ and $Ar^2$ may be attached to the central atom to which they are connected by a single bond, an alkylene, alkenylene or alkynylene group;
$R^3$ is selected from the group consisting of H and aryl, which may be substituted as for $Ar^1$;
$R^4$ and $R^5$ are independently selected from the group consisting of H, alkyl, alkanoyl, benzoyl and benzyl.

25 Claims, No Drawings

AMINO ACID DERIVATIVES

This application is a continuation-in-part of U.S. application Ser. No. 09/128,027, filed Aug. 3, 1998.

The present invention relates to a class of substituted amino acids, to pharmaceutical compositions containing them and to methods of treating neurological and neuropsychiatric disorders using such compounds.

Synaptic transmission is a complex form of intercellular communication that involves a considerable array of specialized structures in both the pre- and post-synaptic terminal and surrounding glial cells (Kanner and Schuldiner, *CRC Critical Reviews in Biochemistry*, 22, 1987:1032). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighbouring synapses, transporters maintain the fidelity of synaptic transmission. Lastly, by sequestering released transmitter into the presynaptic terminal, transporters allow for transmitter reutilization.

Neurotransmitter transport is dependent upon extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., *Neuron*, 11, 1993:401–407). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine also functions in excitatory transmission by modulating the actions of glutamate, the major excitatory neurotransmitter in the central nervous system. See Johnson and Ascher, *Nature*, 325, 1987:529–531; Fletcher et al., *Glycine Transmission*, Otterson and Storm-Mathisen, eds., 1990:193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains two classes of glycine transporters, termed GlyT-1 and GlyT-2. GlyT-1 is found throughout the brain and spinal cord, and it has been suggested that its distribution corresponds to that of glutamatergic pathways and NMDA receptors (Smith, et al., *Neuron*, 8, 1992:927–935). Molecular cloning has further revealed the existence of three variants of GlyT-1, termed GlyT-1a, GlyT-1b and GlyT-1c. Two of these variants (1a and 1b) are found in rodents, each of which displays a unique distribution in the brain and peripheral tissues (Borowsky et al., *Neuron*, 10, 1993:851–863; Adams et al., *J. Neuroscience*, 15, 1995:2524–2532). The third variant, 1c, has only been detected in human tissues (Kim, et al., *Molecular Pharmacology*, 45, 1994:608–617). These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., *J. Biological Chemistry*, 268, 1993:22802–22808; Jursky and Nelson, *J. Neurochemistry*, 64, 1995:1026–1033). Another distinguishing feature of glycine transport mediated by GlyT-2 is that it is not inhibited by sarcosine as is the case for glycine transport mediated by GlyT-1. These data are consistent with the view that, by regulating the synaptic levels of glycine, GlyT-1 and GlyT-2 selectively influence the activity of NMDA receptors and strychnine-sensitive glycine receptors, respectively.

Compounds which inhibit or activate glycine transporters would thus be expected to alter receptor function and, thus, provide therapeutic benefits in a variety of disease states. Inhibition of GlyT-2, for example, can be used to increase the activity of inhibitory neurons having strychnine-sensitive glycine receptors via increasing synaptic levels of glycine, thus diminishing the transmission of pain-related (i.e. nociceptive) information in the spinal cord, which has been shown to be mediated by these receptors (Yaksh, *Pain*, 37, 1989:111–123). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity (Truong et al., *Movement Disorders*, 3, 1988:77–89; Becker, FASEB J, 4, 1990:2767–2774). Spasticity associated with stroke, head trauma, multiple sclerosis, spinal cord injury, dystonia, and other conditions of illness and injury of the nervous system (such as epilepsy) can be treated via modulation of glycine transporters.

Gamma-amino butyric acid (GABA) is the predominant inhibitory neurotransmitter of the central nervous systems and is widely distributed therein. The ionotropic $GABA_A$ and $GABA_C$ receptors and the metabotropic $GABA_B$ receptors mediate GABA activity. $GABA_A$ and $GABA_C$ receptors inhibit neuronal membrane excitability by causing a chloride influx, resulting in hyperpolarization of the neuron. $GABA_B$ receptors are coupled to guanine nucleotide binding proteins (G-proteins). If the G-protein is of the type $G_i$, receptor activation causes the opening of potassium channels, leading to membrane hyperpolarization. If the G-protein is of the class $G_O$, receptor activation retards the opening of calcium channels. $GABA_B$ receptors are commonly found on presynaptic membranes in glutamatergic axon terminals, where the retardation of calcium channel opening inhibits the depolarization-dependent release of glutamate from axon terminals (Costa, *Annu. Rev. Pharmacol. Toxicol.* 38,1998:321–350).

GABA signaling is terminated by the re-uptake of GABA by GABA transporters. Four such transporters have been identified, GAT-1, -2 and -3, and BGT-1 (which also transports betaine) (Miller, Kleven et al., *Neurotransmitter*

Transporters: Structure, Function, and Regulation, Reith ed. 1997:101–150). The GABA transporters are members of the sodium- and chloride-dependent group of transporter gene families. Only GAT-1 and GAT-3 are preferentially localized to the CNS, whereas GAT-2 and BGT-1 are found both in CNS and non-CNS tissues (Ikegaki et al., *Mol. Brain Res.* 26, 1994:47–54, Borden et al., *J. Neurochem.* 64, 1995:977–984, Borden et al., *J. Biol. Chem.* 267, 1992:21098–21104, Liu et al., *J. Biol. Chem.* 268, 1993:2106–2112, Clark et al., *Neuron* 9, 1992:337–348).

Similar to the glycine transporter, compounds which inhibit or enhance the activity of GABA transporters will alter the function of GABA receptors, and, thus, prove useful in the treatment of a variety of disease states.

GABA transmission has been successfully exploited as a target to yield drugs such as benzodiazepines and barbiturates ($GABA_A$ receptor modulators), baclofen ($GABA_B$ receptor agonist) and vigabatrin (GABA transaminase inhibitor). GABA transport modulators will be effective in the treatment of indications for which such compounds have been used, including use as anti-anxiety drugs, anti-epileptics, muscle relaxants and anti-convulsants. For example, the GAT-1 inhibitor, Tiagabine, is marketed as an anticonvulsant.

GABA transport inhibitors will also be useful for the treatment of pain. For example, GABA re-uptake inhibitors have demonstrated analgesic activity and were reported to be more potent than GABA receptor agonists (Zorn and Enna. *Life Sci.* 37 1985:1901–1912). Both GAT-1 and GAT-3 mRNAs were detected in rat in neurons of the periaqueductal gray and spinal cord dorsal horn, and in the thalamus consistent with a role in nociception (Durkin, M M et al. *Mol Brain Res.* 33 1995:7–21).

Evidence also suggests that low GABA levels are linked to depression and possibly mania (Reviewed in Shiah I. S. and Yatham L. N., *Life Sciences,* 63 1998:1289–1303). Animal models of depression indicate a functional correlation of depression with decreased GABA levels. Furthermore, there is some data to suggest that antidepressants like Prozac (Fluoxetine) may, in addition to blocking serotonin uptake, cause an increase in endogenous substances that activate GABA receptors (Uzunove, Sheline et al. *Proc. Natl. Acad. Sci. USA* 95 1990:3239–3244). Thus, compounds which inhibit GABA transport will also be useful for the treatment of depression.

Schizophrenia and other psychoses may have a common link in altered GABA neurotransmission (Keverne, *Brain Res. Bulletin* 48 1999:467–473), suggesting that compounds which alter GABA uptake will be effective antipsychotic agents.

Given that both glycine and GABA are inhibitory neurotransmitters, and that their expression overlaps in many areas of the CNS, compounds with dual activity on both glycine and GABA transporters will be more efficacious than compounds specific for either transporter alone. For example, there is an overlap in expression of GABA, glycine and their receptors in the spinal cord (Todd, A. J. et al., *J. Neuroscience* 16 1996:974–982). A pain-relieving drug which acts at both glycine and GABA transporters will be more effective than a drug which blocks only one of these. In addition, glycine and GABA are implicated in schizophrenia: a compound with dual activity at both glycine and GABA transporters will be a more useful therapeutic agent than a compound which interacts with only one transporter.

Similarly, compounds which inhibit glycine transport via both the GlyT-1 and GlyT-2 glycine transporters will be more effective (in the treatment of, for example, pain and spasticity) than compounds which act at only one of these transporters.

According to one aspect of the invention, there are provided compounds of Formula I:

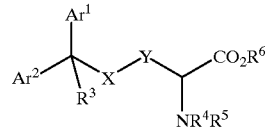

Formula I wherein:
$Ar^1$ and $Ar^2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NRR'$, NRR', $CO_2R$ (where R and R' are independently selected from the group consisting of H and alkyl) and a second aryl group, which may be substituted as above;
wherein any cycloalkyl or aryl substituent is linked to $Ar^1$ or $Ar^2$ by a bridging element which may be a single bond, a vinylene group, an ethynylene group, a Z group, a —Z—$(CH_2)_n$— group, a —$(CH_2)_n$—Z— group, or a —Z—$(CH_2)_n$—Z— group, where Z represents an O atom, a S atom, an NH group or an N-alkyl group, and n is an integer from 1 to 4;
wherein $Ar^1$ and $Ar^2$ may be attached to the central atom to which they are connected by a single bond, an alkylene, alkenylene or alkynylene group;
$R^3$ is selected from the group consisting of H and aryl, which may be substituted as for $Ar^1$;
$R^4$ and $R^5$ are independently selected from the group consisting of H, alkyl, alkanoyl, benzoyl and benzyl;
$R^6$ is selected from the group consisting of H and an alkyl group having up to 20 carbon atoms;
X is selected from the group consisting of S, SO, $SO_2$, NR and CRR', where R and R' are independently selected from the group consisting of H, alkyl, aryl and aralkyl;
Y is a methylene or ethylene bridging element, optionally substituted with one or more substituents independently selected from the group consisting of alkyl and phenyl;
with the following provisos:
when $Ar^1$ and $A^2$ are phenyl rings, $R_3$ is H or a phenyl ring, and $R^4$–$R^6$ are each H, at least one of $Ar^1$ and $Ar^2$ must be substituted;
when X=S and $R^4$–$R^6$ are each H:
(i) Ar2 cannot be unsubstituted phenyl when $Ar^1$ is 4-monosubstituted phenyl;
(ii) $Ar^1$ and $Ar^2$ cannot both be 4-methoxyphenyl when $R^3$ is H or unsubstituted phenyl;
(iii) $Ar^1$, $Ar^2$ and $R^3$ cannot all be 3-fluorophenyl or 4-methoxyphenyl;
(iv) $Ar^1$ and $Ar^2$ cannot both be 4-hydroxymethylphenyl when $R^3$ is unsubstituted phenyl
and a stereoisomer, salt, solvate and hydrate thereof.

Compounds of the invention inhibit glycine transport. Certain compounds of the invention inhibit such transport via both the GlyT-1 and GlyT-2 transporters. Still other compounds of the invention inhibit the uptake of δ-aminobutyric acid (GABA) via the GAT-1 transporter as well as glycine uptake via the GlyT-2 transporter. Preferred are those compounds which selectively inhibit glycine transport, and which do so via the GlyT-2 transporter. By GlyT-2 we mean those glycine transporters found predominantly in the brain stem and spinal cord and the distribution of which corresponds closely to that of strychnine-sensitive glycine receptors (Liu et al. *J. Biological Chemistry*, 268, 1993:22802–22808; Jursky and Nelson, *J. Neurochemistry*, 64,1995:1026–1033).

According to another aspect of the invention, there is provided a pharmaceutical composition comprising a compound of Formula I in an amount effective to inhibit glycine transport, and a pharmaceutically acceptable carrier.

In another aspect of the present invention there are provided compositions containing the present compounds in amounts for pharmaceutical use to treat medical conditions for which a glycine transport inhibitor is indicated. Preferred are those compositions containing compounds useful in the treatment of medical conditions for which GlyT-2-mediated inhibition of glycine transport is needed, such as the treatment of pain, epilepsy or conditions associated with increased muscle contraction.

These and other aspects of the present invention are described in greater detail hereinbelow.

DEFINITIONS

The term aryl as used herein means a monocyclic aromatic group such as phenyl, pyridyl, furyl, thienyl and the like, or a bicyclic benzo-fused aromatic group such as naphthyl, indanyl, quinolinyl and the like.

The term alkyl as used herein means straight- and branched-chain alkyl radicals containing from one to six carbon atoms and includes methyl, ethyl and the like.

The term cycolalkyl as used herein means a carbocyclic ring containing from three to eight carbon atoms and includes cyclopropyl, cyclohexyl and the like.

The terms aralkyl and aralkyloxy as used herein means an alkyl radical substituted with an aryl or aryloxy group and includes benzyl, phenethyl, benzyloxy and the like.

The terms alkylene, alkenylene and alkynylene as used herein means straight- and branched-chain bivalent radicals containing from one to six carbon atoms, such as methylene, ethylene, vinylene, propenylene and ethynylene.

The term alkoxy as used herein means straight- and branched-chain alkoxy radicals containing from one to six carbon atoms and includes methoxy, ethoxy and the like.

The term alkanoyl as used herein means straight- and branched-chain radicals containing from one to six carbon atoms and includes acetyl, propionyl and the like.

The term halo as used herein means halogen and includes fluoro, chloro, bromo and the like.

DETAILED DESCRIPTION AND PREFERRED EMBODIMENTS

Compounds of Formula I include those in which $Ar^1$ and $Ar^2$ are, independently, optionally-substituted aryl groups. Preferably, $Ar^1$ is optionally-substituted phenyl, more preferably alkyl-substituted phenyl. Even more preferably, $Ar^1$ is a 3,4-diethylphenyl group. Most preferably, $Ar^1$ is a 6-(1,2,3,4-tetrahydronaphthyl) group. Preferably, $Ar^2$ is optionally-substituted phenyl, more preferably halo-substituted phenyl and, even more preferably, $Ar^2$ is a 4-fluorophenyl group. Most preferably, $Ar^2$ is a 2,4-difluorophenyl group.

The compounds of Formula I include those in which $R^3$ is selected from the group consisting of H and an optionally substituted aryl group. Preferably, $R^3$ is selected from the group consisting of H and optionally-substituted phenyl and, more preferably, $R^3$ is H.

Formula I compounds also include those in which $R^4$–$R^6$ are selected from the group consisting of H and alkyl, preferably H and methyl. In preferred embodiments, $R^4$–$R^6$ are all H.

In specific embodiments of the invention, the compounds of Formula I include:
S-(4-Ethyl-4'-fluorodiphenyl)methyl-D,L-cysteine;
S-(3,4-Diethyl-4'-fluorodiphenyl)methyl-D,L-cysteine;
S-(3,4-Diethyl-4'-fluorodiphenyl)methyl-L-cysteine;
S-(2,4-Difluoro-4'-ethyidiphenyl)methyl-D,L-cysteine;
S-(3,4-Diethyldiphenyl)methyl-D,L-cysteine;
S-(2,4-Difluoro-4'-n-propyidiphenyl)methyl-D,L-cysteine;
S-(4-Ethyldiphenyl)methyl-D,L-cysteine;
S-(4-Ethyl-3'-fluorodiphenyl)methyl-D,L-cysteine;
S-(3-Fluoro-4'-n-propyldiphenyl)methyl-D,L-cysteine;
S-(4-t-Butyldiphenyl)methyl-D,L-cysteine;
S-(2'-Chloro-3,4-diethyl-4'-fluorodiphenyl)methyl-L-cysteine;
S-(3,4-Diethyl-2'-fluoro-4'-trifluoromethyldiphenyl)methyl-L-cysteine;
S-(4'-Chloro-3,4-diethyl-2'-fluorodiphenyl)methyl-L-cysteine;
S-(3,4-Diethyl-2'-fluoro-4'-methoxydiphenyl)methyl-L-cysteine;
S-(3,4-Diethyl-3',4'-difluorodiphenyl)methyl-D,L-cysteine;
S-(3,4-Diethyl-2',4'-difluorodiphenyl)methyl-D,L-cysteine;
S-(3,4-Diethyl-3'-fluorodiphenyl)methyl-D,L-cysteine;
S-(3,4-Diethyl-2'-fluorodiphenyl)methyl-D,L-cysteine;
S-(3,4-Diethyl-2'4'-difluorodiphenyl)methyl-L-cysteine;
S-(3,4-Diethyl-3',5'-difluorodiphenyl)methyl-L-cysteine;
S-(3,4-Diethyl-2',6'-difluorodiphenyl)methyl-L-cysteine;
S-(3,4-Diethyl-3',4'-difluorodiphenyl)methyl-L-cysteine;
S-(3,4-Diethyl-3'-fluorodiphenyl)methyl-L-cysteine;
S-(3,4-Diethyl-2'-fluorodiphenyl)methyl-L-cysteine;
S-(3,3',4,4'-Tetramethyldiphenyl)methyl-L-cysteine;
S-(R)-(3,4-Diethyl-4'-fluorodiphenyl)methyl-L-cysteine;
S-(S)-(3,4-Diethyl-4'-fluorodiphenyl)methyl-L-cysteine;
S-(4-Ethyl-4'-fluorodiphenyl)methyl-L-cysteine;
S-(3,4-Diethyl-4'-fluorodiphenyl)methyl-L-penicillamine;
S-(2,4-Dichlorodiphenyl)methyl-D,L-cysteine;
S-(2,4-Dichlorodiphenyl)methyl-D,L-homocysteine;
S-(2,4-Difluoro-3',4'-methylenedioxydiphenyl)methyl-D,L-cysteine;
S-(2-Benzyloxydiphenyl)methyl-D,L-cysteine;
S-(2-Iododiphenyl)methyl-D,L-cysteine;
S-(2-Phenyidiphenyl)methyl-D,L-cysteine;
S-(3-Fluoro-4'-"propyldiphenyl)methyl-D,L-cysteine;
S-(3-Fluoro-4-trifluoromethyidiphenyl)methyl-D,L-homocysteine;
S-[4,4'-Di-(dimethylamino)diphenyl]methyl-D,L-cysteine;
S-[4,4'-Di-(trifluoromethyl)diphenyl]methyl-D,L-homocysteine;
S-(4,4'-Dichlorodiphenyl)methyl-D,L-cysteine;
S-(4,4'-Dichlorodiphenyl)methyl-D,L-homocysteine;
S-(4,4'-Difluorodiphenyl)methyl-D,L-cysteine;
S-(4-Chloro-3',4'-diethyl-2-fluorodiphenyl)methyl-D,L-cysteine;
S-(4-Fluoro-2'-phenyidiphenyl)methyl-D,L-cysteine;
S-(4-Fluoro-3-trifluoromethyl-diphenyl)methyl-D,L-cysteine;
S-(4-Fluoro-3-trifluoromethyldiphenyl)methyl-D,L-homocysteine;
S-(4-Nitrodiphenyl)methyl-D,L-cysteine;
S-[α-(1-Naphthyl)α-(4-fluorophenyl)]methyl-D,L-cysteine;
S-[α-(2-(4-Methoxybenzyloxy)phenyl)-α-phenyl]methyl-D,L-cysteine;
S-[α-(2-Methoxy-1-naphthyl)-α-(3-methylphenyl)]methyl-D,L-cysteine;
S-[α-(4-Methoxy-1-naphthyl)-α-(3-methylphenyl)]methyl-D,L-cysteine;
S-[α-(Indan-5-yl)-α-(2,4-difluorophenyl)]methyl-D,L-cysteine;

S-[α-(Indan-5-yl)-α-(4-fluorophenyl)]methyl-D,L-cysteine;
S-[α-(Indan-5-yl)-α-(phenyl)]methyl-D,L-cysteine;
S-[α,α-Bis(5-methyl-2-thienyl)]methyl-D,L-cysteine;
2-Amino-3-(diphenylamino)-propanoic acid;
2-Amino-5,5-di-(4-isopropylphenyl)-pentanoic acid;
S-(4-ᵗButyidiphenyl)methyl-D,L-homocysteine;
S-(3,4-Diethyl-2,4-difluorodiphenyl)methyl-D,L-homocysteine;
S-(3,4-Diethyl-2-fluorodiphenyl)methyl-D,L-homocysteine;
S-(3,4-Diethyl-3,4-difluorodiphenyl)methyl-D,L-homocysteine;
S-(3,4-Diethyl-3-fluorodiphenyl)methyl-D,L-homocysteine;
S-(3-Benzyloxydiphenyl)methyl-D,L-cysteine;
S-(2-Benzyloxy-2'-fluorodiphenyl)methyl-D,L-cysteine; and
S-[2-Fluoro-2'-(2-fluorobenzyloxy)diphenyl]methyl-D,L-cysteine.

In preferred embodiments the invention, the compounds of Formula I include:
S-(4-ᵗButyldiphenyl)methyl-D,L-cysteine;
S-(4,4'-Diisopropyldiphenyl)methyl-D,L-cysteine;
S-(4,4'-Dimethyidiphenyl)methyl-D,L-cysteine;
S-(2,2',3,3',5,5',6,6'-Octamethyldiphenyl)methyl-D,L-cysteine;
S-(2,2',3,3',5,5'-Hexamethyidiphenyl)methyl-D,L-cysteine;
S-(2,2',4,4',6,6'-Hexamethyidiphenyl)methyl-D,L-cysteine;
S-(2,2',4,4'-Tetramethyldiphenyl)methyl-D,L-cysteine;
S-(2,2',5,5'-Tetramethyldiphenyl)methyl-D,L-cysteine;
S-(2,3-Diethyl-2'-fluoro-4'-methoxydiphenyl)methyl-D,L-cysteine and
S-(3,3',4,4'-Tetraethyidiphenyl)methyl-D,L-cysteine.

In more preferred embodiments of the invention, the compounds of Formula I include:
S-(3,4-Diethyl-4'-fluorodiphenyl)methyl-D,L-ysteine;
S-(3,4-Diethyl-4'-fluorodiphenyl)methyl-L-cysteine;
S-(4-Ethyl-4'-fluorodiphenyl)methyl-L-cysteine;
S-(3,4-Diethyl-2',4'-difluorodiphenyl)methyl-D,L-cysteine;
S-(3,4-Diethyl-2',4'-difluorodiphenyl)methyl-L-cysteine;
S-(3,4-Diethyl-4'-fluorodiphenyl)methyl-D,L-cysteine;
S-(3,4-Diethyl-4'-fluorodiphenyl)methyl-L-cysteine;
S-(4-Ethyl-4'-fluorodiphenyl)methyl-L-cysteine;
S-(2,4-Difluoro-4'-ethyldiphenyl)methyl-D,L-cysteine;
S-(3,4-Diethyldiphenyl)methyl-D,L-cysteine;
S-(2,4-Difluoro-4'-n-propyidiphenyl)methyl-D,L-cysteine;
S-(4-Ethyldiphenyl)methyl-D,L-cysteine;
S-(4-Ethyl-4'-fluorodiphenyl)methyl-D,L-cysteine;
S-(3,4-Diethyl-2',4'-difluorodiphenyl)methyl-D,L-cysteine, methyl ester;
S-(3,4-Diethyl-2',4'-difluorodiphenyl)methyl-D,L-dimethylcysteine;
S-(3,4-Diethyl-2'-fluorodiphenyl) methyl-D,L-dimethylcysteine;
S-(3,4-Diethyl-2'-methoxydiphenyl)methyl-D,L-cysteine;
S-(3,4-Diethyl-2'-methoxydiphenyl)methyl-D,L-cysteine, methyl ester;
S-(3,4-Diethyl-2'-nitrodiphenyl)methyl-D,L-cysteine;
S-(3,4-Diethyl-2'-trifluoromethyldiphenyl)methyl-D,L-cysteine;
S-(3,4-Diethyl-3',4'-difluorodiphenyl)methyl-D,L-dimethylcysteine;
S-(3,4-Diethyl-3'-fluorodiphenyl)methyl-D,L-dimethylcysteine;
S-(3,4-Diethyl-3'-fluorodiphenyl)methyl-D,L-dimethylcysteine;
S-(3,4-Diethyl-3'-trifluoromethyldiphenyl)methyl-D,L-cysteine;
S-(3,4-Diethyl-4'-fluorodiphenyl)methyl-D,L-cysteine;
S-(3,4-Diethyl-4'-nitrodiphenyl)methyl-D,L-cysteine, methyl ester;
S-(3,4-Diethyl-4'-nitrodiphenyl)methyl-D,L-cysteine;
S-(3,4-Diethyl-4'-trifluoromethyldiphenyl)methyl-D,L-cysteine;
S-(3,4-Diethylphenyl-2',4'-difluorodiphenyl)methyl-N-methyl-D,L-cysteine and
S-(3,4-Diethylphenyl-2',4'-difluorodiphenyl)methyl-N-methyl-N-methyl-D,L-cysteine, methyl ester.

In the most preferred embodiments of the invention, the compounds of Formula I include:
S-[(+)-(3,4-diethyl-4'-fluorodiphenyl)methyl]-L-cysteine;
S-[α-(5,6,7,8-Tetrahydro-2-naphthyl)-α-(2,4-difluorophenyl)]methyl-D,L-cysteine;
S-[α-(5,6,7,8-Tetrahydro-5,5,8,8-tetramethyl-2-naphthyl)-α-(2,4-difluorophenyl)]methyl-D,L-cysteine;
S-[α-(5,6,7,8-Tetrahydronaphth-2-yl)-α-(2,4-difluorophenyl)]methyl-D,L-cysteine;
S-[α-(5,6,7,8-Tetrahydronaphth-2-yl)-α-(2-nitrophenyl)]methyl-N-methyl-D,L-cysteine;
S-[α-(5,6,7,8-Tetrahydronaphth-2-yl)-α-(3-trifluoromethylphenyl)]methyl-N-methyl-D,L-cysteine and
S-[α-(5,6,7,8-Tetrahydronaphth-2-yl)-α-(4-cyanophenyl)]methyl-N-methyl-D,L-cysteine.

Compounds of Formula I can be considered to be amino acids or derivatives thereof. Compounds which contain, instead of a carboxylate group, a "carboxylate equivalent" group, such as hydroxamic acids, phosphonic acids, phosphinic acids, sulfonic acids, sulfinic acids, amides or tetrazoles are also considered an embodiment of the present invention.

In another embodiment of the invention, the compound of Formula I is provided in labeled form, such as radiolabeled form, e.g. labeled by incorporation within its structure $^3$H or $^{14}$C or by conjugation to $^{125}$I. In a preferred aspect of the invention, those compounds which bind preferentially to GlyT-2 versus GlyT-1 can be used, in labeled form, to identify GlyT-2 transporter ligands by techniques common in the art. This can be achieved by incubating the transporter or tissue in the presence of a ligand candidate and then incubating the resulting preparation with an equimolar amount of radiolabeled compound of the invention. GlyT-2 transporter ligands are thus revealed as those that are not significantly displaced by the radiolabeled compound of the present invention. Alternatively, GlyT-2 transporter ligand candidates may be identified by first incubating a radiolabeled form of a compound of the invention then incubating the resulting preparation in the presence of the candidate ligand. A more potent GlyT-2 transporter ligand will, at equimolar concentration, displace the radiolabeled compound of the invention.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention.

The conversion of a given compound salt to a desired compound salt is achieved by applying standard techniques, well known to those skilled in the art.

The compounds of the present invention have at least one chiral centre. The invention extends to cover all structural and optical isomers of these compounds, as well as to racemic mixtures thereof.

The compounds of the present invention which are derived from the amino acid cysteine (i.e. compounds of Formula I where X=S and Y is a methylene-based bridge) can be prepared by processes analogous to those established in the art. Such compounds are readily prepared utilizing, for example, the method shown in Scheme 1.

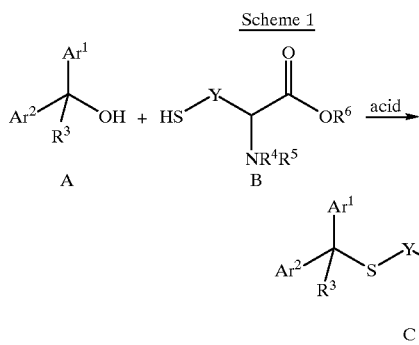

Scheme 1

An alcohol of Formula A, wherein $Ar^1$, $Ar^2$ and $R^3$ are as defined in Formula I, is condensed with cysteine or a cysteine derivative of Formula B (where $R^4$–$R^6$ are as defined in Formula I) in the presence of an acid either neat or in an inert solvent and at temperatures in the range of 0–50° C. Suitable acids include trifluoroacetic acid, p-toluenesulfonic acid, camphorsulfonic acid and the like and suitable solvents include methylene chloride, chloroform, toluene and the like. Preferred reaction conditions are neat trifluoroacetic acid at room temperature. The amino functionality of compounds of Formula C wherein $R^4$ and $R^5$ are H may be derivatized by standard alkylation or reductive amination procedures, to provide compounds of Formula I wherein $R^4$ and $R_5$ are $C_{1-4}$alkyl and the remaining groups are as defined above.

If necessary, the cysteine amino group (i.e. $NR^4R^5$, where at least one of $R^4$ or $R^5$ is H) can be protected, for example by making an acid-stable derivative such as a 9-fluorenylmethoxycarbonyl (Fmoc) derivative, which can then undergo the coupling reaction described above. The protecting group can be removed by treatment with a mild base such as piperidine (either neat, or in an inert solvent). Use of such protected cysteines is preferred, as the coupling reaction proceeds with higher yield, and gives a cleaner product.

If desired, hydrolysis of the ester functionality of the resulting compounds using non-acidic conditions provides compounds of Formula I wherein $R^6$ is H and the remaining groups are as defined above.

Penicillamine analogs were prepared in a similar fashion to that shown in Scheme 1, the coupling reaction being carried out with an appropriate penicillamine instead of cysteine B.

Alternatively, cysteine-derived compounds of the invention may also be prepared as shown in Scheme 2.

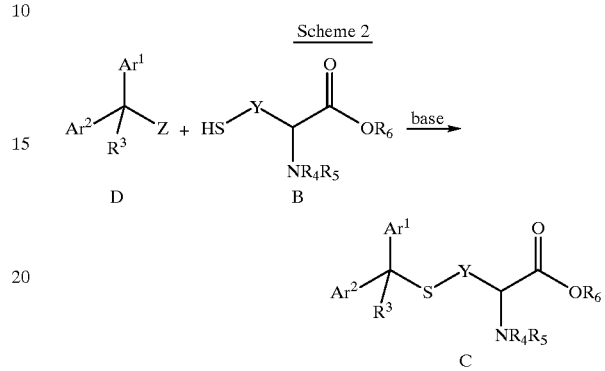

Scheme 2

Reagents of Formula D, wherein $Ar^1$, $Ar^2$ and $R^3$ are as defined in Formula I and Z is an appropriate leaving group such as halo or mesylate may be treated with a cysteine derivative of Formula B, wherein $R^4$–$R^6$ are as defined above, in the presence of a mild base such as sodium carbonate in an inert solvent such as dimethylformamide. Manipulation of the protected amino group may be performed as described above, and carboxylate esters can be hydrolyzed in the standard fashion.

Diphenylmethanols A are either commercially available or may be prepared using standard procedures, for example by hydride reduction of the corresponding benzophenones or reaction of organometallic compounds with aromatic aldehydes. Reagents D are either commercially available, or are prepared by reaction of the corresponding diphenylmethanol with, for example, thionyl chloride. The benzophenones may be purchased or prepared by standard Friedel-Crafts acylation of a substituted benzene with a substituted benzoyl halide.

Homocysteines B (i.e. compounds of Formula 1 where X is a sulfur atom and Y is an ethylene bridge) were prepared in an analogous fashion to that shown in Schemes 1 and 2, using the appropriate homocysteine in place of cysteine B.

Compounds of the invention in which X represents an amino group can be prepared as shown in Scheme 3.

Scheme 3

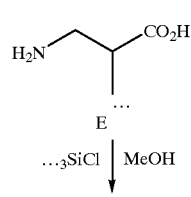

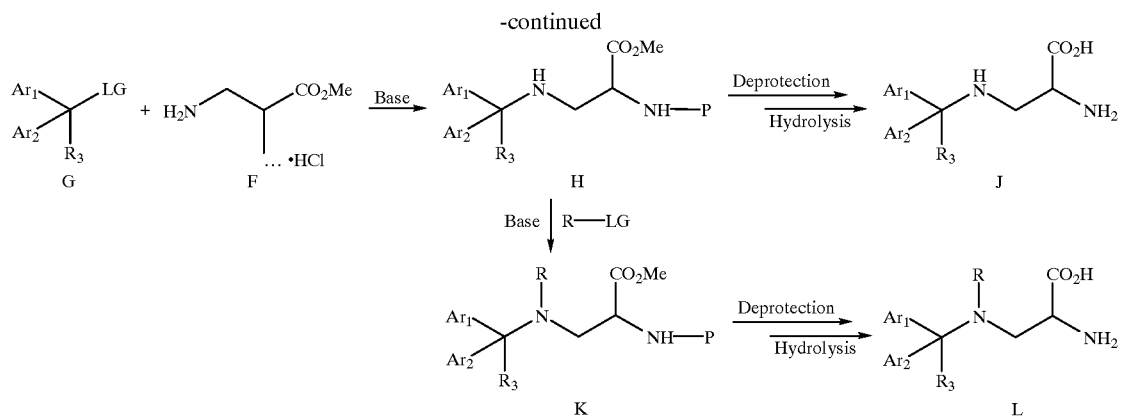

N-protected (NH-P in Scheme 3) diaminopropionic acid E (for example N-α-Fmoc-L-α,β-diaminopropionic acid) is esterified to give intermediate F which, when coupled with compound G (in which LG is a leaving group such as halo or mesylate) under mildly basic conditions (such as sodium carbonate) gives intermediate H. Deprotection of the amino functionality (using, for example, piperidine) and hydrolysis of the ester group (using, for example, aqueous sodium hydroxide in methanol) gives product J.

N-alkylated compounds L can also be prepared from intermediate H, by treatment with an alkyl halide (or otherwise activated alkyl compound) in the presence of a mild base (such as potassium carbonate) or, alternatively, by reductive amination with an appropriate aldehyde. Intermediate K can then be deprotected and hydrolysed as above to give the desired product.

Compounds of Formula 1 in which X is a carbon atom and Y is a methylene bridge were prepared as shown in Scheme 4.

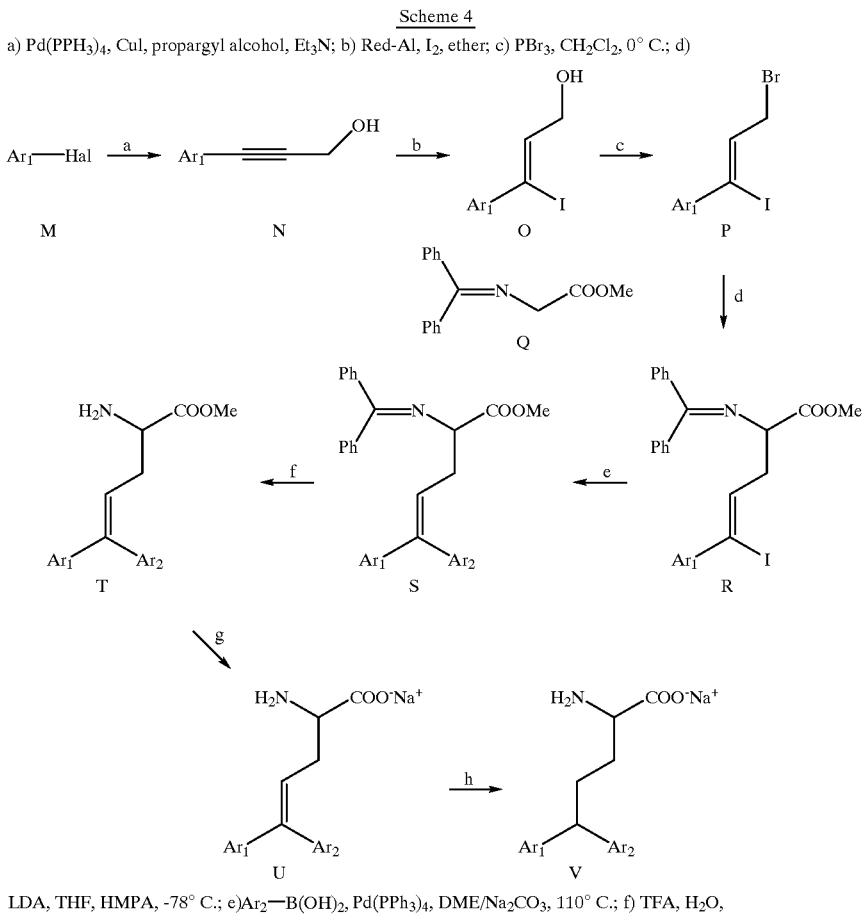

Scheme 4
a) Pd(PPH$_3$)$_4$, CuI, propargyl alcohol, Et$_3$N; b) Red-Al, I$_2$, ether; c) PBr$_3$, CH$_2$Cl$_2$, 0° C.; d) LDA, THF, HMPA, -78° C.; e) Ar$_2$—B(OH)$_2$, Pd(PPh$_3$)$_4$, DME/Na$_2$CO$_3$, 110° C.; f) TFA, H$_2$O, CH$_2$Cl$_2$, rt; g) 1N NaOH, MeOH; h) H$_2$, 10% Pd/C, EtOH.

Such compounds can also be prepared as shown in Scheme 5.

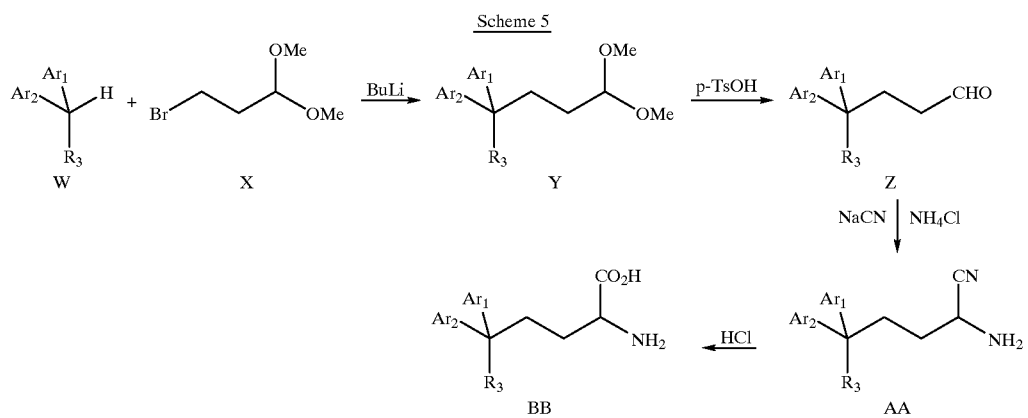

Treatment of starting material W with butyl lithium, followed by bromoacetal X gives intermediate Y which, upon deprotection gives aldehyde Z (which is also accessible from compound W by treatment with (optionally-protected) 3-bromopropanol and butyl lithium, followed by Swern oxidation of the resulting alcohol). A Strecker reaction gives nitrile AA which can be hydrolysed to give amino acid product BB.

Compounds of the invention which contain so-called "carboxylate equivalents" (as previously defined) can be prepared in a variety of ways. For example, hydroxamic acids can be prepared from the corresponding carboxylic acids by conversion to an N-hydroxysuccinimide ester followed by treatment with hydroxylamine. Amides are accessible by treatment of a methyl ester with ammonia in methanol. Tetrazoles wherein X is a CRR' group can be prepared by reacting α-cyanohydroxyimines with sodium azide, followed by hydrogenation (see Lunn et al., *J. Med. Chem.*, 35, 4608 (1992)).

Phosphonate analogues are accessible by a number of routes, for example those shown in Schemes 6 to 9. For those compounds of Formula 1 where X is carbon, aldehyde Z, upon treatment with benzyl carbamate and triphenyl phosphite in acetic acid (Oleksyszyn et al., *Synthesis*, 985–986, 1979; Jackson et al., *J. Med. Chem.*, 41, 2289–2301, 1988) gives intermediate CC which, upon hydrogenation and base hydrolysis, gives phosphonate DD, as shown in Scheme 6.

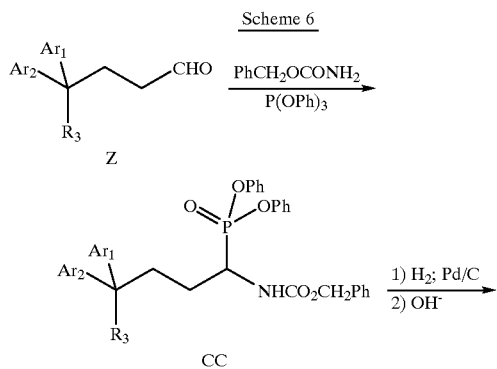

-continued

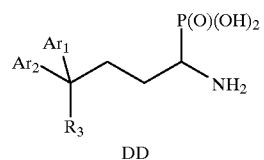

For the corresponding O, S and N analogues, the routes shown in Schemes 7 to 9 can be used. Phosphonate reagents FF, KK and OO may be prepared according to methods disclosed in Engel et al., *Organic Reactions Volume* 36, p 195.

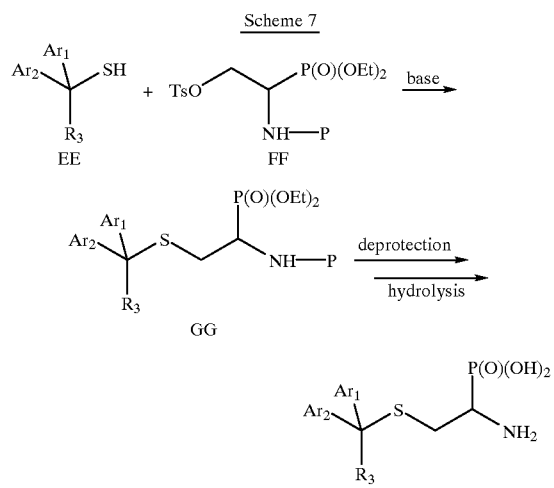

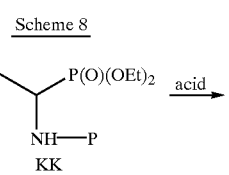

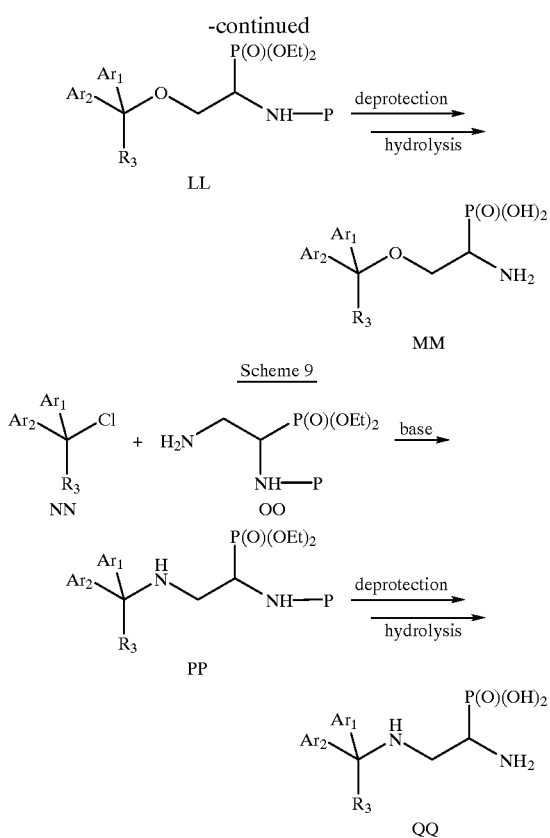

The present compounds are useful as pharmaceuticals for the treatment of various conditions in which the use of a glycine transport inhibitor is indicated. Certain compounds of the invention are useful as pharmaceuticals for the treatment of conditions in which the use of a mixed GlyT-2 glycine transport inhibitor and GAT inhibitor is indicated, and still other compounds of the invention are useful as pharmaceuticals for the treatment of various conditions in which the use of a mixed GlyT-1 and GlyT-2 glycine transport inhibitor is indicated is indicated.

Preferred compounds are those useful as pharmaceuticals for the treatment of medical conditions for which GlyT-2-mediated inhibition of glycine transport is needed, such as the treatment of pain or the treatment of diseases or conditions associated with increased muscle contraction, for example spasticity and myoclonus. Spasticity that can be treated via modulation of glycine transporters is that associated with epilepsy, stroke, head trauma, multiple sclerosis, spinal cord injury, dystonia, and other conditions of illness and injury of the nervous system. By GlyT-2 we mean those glycine transporters found predominantly in the brain stem and spinal cord and the . distribution of which corresponds closely to that of strychnine-sensitive glycine receptors (Liu et al. *J. Biological Chemistry*, 268, 1993:22802–22808; Jursky and Nelson, *J. Neurochemistry*, 64, 1995:1026–1033).

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 1 to 25 mg) of a compound of Formula I or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous or intramuscular dose of between 0.1 mg and 100 mg, preferably between 0.1 mg and 50 mg, e.g., between 1 mg and 25 mg, of a compound of Formula I or a pharmaceutically acceptable salt, solvate or hydrate thereof calculated as the free base, the compound being administered 1 to 4 times per day. Suitably, the compounds will be administered for a period of continuous therapy, for example for a week or more.

Experimental Examples (i) Benzoic Acids

4-Chloro-2-fluorobenzoic acid was synthesized by $KMnO_4$ oxidation of 4-chloro-2-fluorotoluene (Clarke, H. T.; Taylor, E. R., Org. Synth. Coll. Vol II, 135–136).

2-Fluoro-4-methoxybenzoic acid was synthesized by $KMnO_4$ oxidation of 2-fluoro-4-methoxyacetophenone (Clarke, H. T.; Taylor, E. R., Org. Synth. Coll. Vol II, 135–136).

(ii) Benzoyl Chlorides

Benzoyl Chlorides were either purchased or synthesized from the corresponding benzoic acid derivatives by reacting with $SOCl_2$. The following benzoyl chlorides were prepared in this manner:
2-Chloro-4-fluorobenzoyl chloride;
4-Chloro-2-fluorobenzoyl chloride;
2-Fluoro-4-methoxybenzoyl chloride; and
2-Fluoro-4-trifluoromethylbenzoyl chloride.

(iii) Benzophenones

EXAMPLE 1

3,4-Diethylbenzophenone

A mixture of benzoyl chloride (1 eq) and 3,4-diethylbenzene (1.15 eq) was dissolved in 1,2-dichloroethane in a dry flask under argon and cooled in an ice bath with stirring. Aluminum chloride (1.3 eq) was added in portions to the reaction mixture at a rate to maintain the temperature below 10° C. Upon complete addition of the aluminum chloride, the ice bath was removed and the reaction mixture was stirred at room temperature for 18 h, then poured into cold water (100 mL) and extracted into ether (2×100 mL). The combined ether extracts were washed with water (25 mL), sodium bicarbonate solution (2×25 mL), water (25 mL), brine (25 mL), dried ($MgSO_4$) and concentrated to provide the title compound as an oil.

In a like manner, the following additional compounds were prepared. Any regioisomers formed were separated using silica gel chromatography.
4-Ethyl-4'-fluorobenzophenone;
3,4-Diethyl-4'-fluorobenzophenone;
2,4-Difluoro-4'-ethylbenzophenone;
4-Ethyl-3'-fluorobenzophenone;
2,4-Difluoro-4'-n-propylbenzophenone;
3-Fluoro-4'-n-propylbenzophenone;
2'-Chloro-3,4-diethyl-4'-fluorobenzophenone;
3,4-Diethyl-2'-fluoro-4'-trifluoromethylbenzophenone;
4'-Chloro-3,4-diethyl-2'-fluorobenzophenone;
3,4-Diethyl-2'-fluoro-4'-methoxybenzophenone;
3,4-Diethyl-3',4'-difluorobenzophenone;
3,4-Diethyl-2',4'-difluorobenzophenone;
3,4-Diethyl-3'-fluorobenzophenone;
3,4-Diethyl-2'-fluorobenzophenone;
3,4-Diethyl-4',2'-difluorobenzophenone;
3,4-Diethyl-3',5'-difluorobenzophenone;
3,4-Diethyl-2',6'-difluorobenzophenone;
3,4-Diethyl-3',4'-difluorobenzophenone;
3,4-Diethyl-3'-fluorobenzophenone;
3,4-Diethyl-2'-fluorobenzophenone; and
3,3',4,4'-Tetramethylbenzophenone.

(iv) Diphenylmethanols

EXAMPLE 2

4-Ethyl-4'-fluorodiphenylmethanol

To a suspension of 4-ethyl-4'-fluorobenzophenone (Example 1b, 6.8 g, 30 mmol) in absolute ethanol (200 mL) was added sodium borohydride (1.15 g, 30 mmol). The mixture was stirred at room temperature for 18 hours, concentrated to a white solid and suspended in water (150 mL) and ether (150 mL). The ether fraction was separated and the aqueous fraction was extracted with another portion of ether (150 mL). The combined ether fractions were washed with water (3×100 mL), brine (100 mL), dried ($Na_2SO_4$) and concentrated to provide the title compound as a white solid (6.21 g, 90%) which was used for subsequent reactions without further purification.

In a corresponding manner, the following additional compounds were prepared:
3,4-Diethyl-4'-fluorodiphenylmethanol;
2,4-Difluoro-4'-ethyidiphenylmethanol;
3,4-Diethyidiphenylmethanol;
2,4-Difluoro-4'-n-propyldiphenylmethanol;
4-Ethyidiphenylmethanol;
4-Ethyl-3'-fluorodiphenylmethanol;
3-Fluoro-4'-n-propyidiphenylmethanol;
4-t-Butyldiphenylmethanol;
2'-Chloro-3,4-diethyl-4'-fluorodiphenylmethanol;
3,4-Diethyl-2'-fluoro-4'-trifluoromethyidiphenylmethanol;
4'-Chloro-3,4-diethyl-2'-fluorodiphenylmethanol;
3,4-Diethyl-2'-fluoro-4'-methoxydiphenylmethanol;
3,4-Diethyl-3',4'-difluorodiphenylmethanol;
3,4-Diethyl-2',4'-difluorodiphenylmethanol;
3,4-Diethyl-3'-fluorodiphenylmethanol;
3,4-Diethyl-3',5'-difluorodiphenylmethanol;
3,4-Diethyl-2',6'-difluorodiphenylmethanol;
3,4-Diethyl-2'-fluorodiphenylmethanol; and
3,3',4,4'-Tetramethyidiphenylmethanol.

Alternatively, diphenylmethanols were prepared by a Grignard reaction between an arylmagnesium halide and an appropriately substituted aldehyde, according to the following general procedure:

A solution of 4mmol of an arylaldehyde in 16 mL of anhydrous THF was treated with 5 mL of a 1.0M commercially available or freshly prepared arylmagnesium bromide at 0° C. under $N_2$. The mixture was warmed to room temperature and the reaction quenched after 2 h by the addition of 30 mL of saturated $NH_4Cl$ solution. The mixture was extracted with 2×50 mL of ether and the combined ether fractions washed with 25 mL of $H_2O$, 25 mL of brine, dried ($MgSO_4$) and concentrated. Generally, the products were used without additional purification. However, the products can be purified by $SiO_2$ biotage chromatography, if desired. Grignard reagents were prepared by vigorously stirring a mixture of 132 mg (5.5 mmol) of Mg, 5 mL of anhydrous THF and 5 mmol of an aryl bromide under $N_2$ for 2 to 18 h.

In this manner, the following compounds were prepared:
2-Benzyloxydiphenylmethanol;
2-(4-Methoxybenzyloxy)diphenylmethanol;
α-(1-Naphthyl)-α-4-fluorophenylmethanol;
α-[1-(2-Methoxynaphthyl)]-α-(3-tolyl)methanol;

4-Fluoro-2'-phenyldiphenylmethanol,
2-phenyldiphenylmethanol;
3,4-Diethyl-2',4'-difluorophenylmethanol; and
α,α-Di-(5-methyl-2-thienyl)methanol.

(v) S-Diphenylmethyl-L-cysteines

EXAMPLE 3

S-(4-Ethyl-4'-fluorodiphenyl)methyl-L-cysteine

Prepared according to the procedure of Photaki, I et al. *J. Chem. Soc.* 1970:2683–2697. A mixture of 4-ethyl-4'-fluorodiphenylmethanol (Example 2a, 0.33 g, 1 mmol) and L-cysteine (0.12 g, 1 mmol) were combined in a dry 50 mL flask flushed with argon. Anhydrous trifluoroacetic acid (2 mL) was added and the flask was stoppered and gently swirled by hand until all the material went into solution. The dark brown solution was left to stand at room temperature for 10 to 15 minutes, then concentrated to an oil which was taken up in ether (30 mL) and treated with saturated sodium bicarbonate (15 mL). A thick precipitate formed upon shaking the mixture, which was filtered, washed with water (2×15 mL), acetone (2×5 mL) and ether (2×10 mL) to give 0.24 g (72%) of a light yellow powder.

In a corresponding manner, the following additional compounds were prepared:
S-(3,4-Diethyl-4'-fluorodiphenyl)methyl-D,L-cysteine;
S-(3,4-Diethyl-4'-fluorodiphenyl)methyl-L-cysteine;
S-(2,4-Difluoro-4'-ethyldiphenyl)methyl-D,L-cysteine;
S-(3,4-Diethyldiphenyl)methyl-D,L-cysteine;
S-(2,4-Difluoro-4'-n-propyldiphenyl)methyl-D,L-cysteine;
S-(4-Ethyldiphenyl)methyl-D,L-cysteine;
S-(4-Ethyl-3'-fluorodiphenyl)methyl-D,L-cysteine;
S-(3-Fluoro-4'-n-propyldiphenyl)methyl-D,L-cysteine;
S-(3,4-Diethyl-4'-fluorodiphenyl)methyl-L-penicillamine;
S-(4-t-Butyldiphenyl)methyl-D,L-cysteine;
S-(2'-Chloro-3,4-diethyl-4'-fluorodiphenyl)methyl-L-cysteine;
S-(3,4-Diethyl-2'-fluoro-4'-trifluoromethyidiphenyl)methyl-L-cysteine;
S-(3,4-Chloro-3,4-diethyl-2'-fluorodiphenyl)methyl-L-cysteine;
S-(3,4-Diethyl-2'-fluoro-4'-methoxydiphenyl)methyl-L-cysteine;
S-(3,4-Diethyl-3',4'-difluorodiphenyl)methyl-D,L-cysteine;
S-(3,4-Diethyl-2',4'-difluorodiphenyl)methyl-D,L-cysteine;
S-(3,4-Diethyl-3'-fluorodiphenyl)methyl-D,L-cysteine;
S-(3,4-Diethyl-2'-fluorodiphenyl)methyl-D,L-cysteine;
S-(3,4-Diethyl-4',2'-difluorodiphenyl)methyl-L-cysteine;
S-(3,4-Diethyl-3',5'-difluorodiphenyl)methyl-L-cysteine;
S-(3,4-Diethyl-2',6'-difluorodiphenyl)methyl-L-cysteine;
S-(3,4-Diethyl-3',4'-difluorodiphenyl)methyl-L-cysteine;
S-(3,4-Diethyl-3'-fluorodiphenyl)methyl-L-cysteine;
S-(3,4-Diethyl-2'-fluorodiphenyl)methyl-L-cysteine;
S-(3,3',4,4'-Tetramethyldiphenyl)methyl-L-cysteine;
S-(4-Ethyl-4'-fluorodiphenyl)methyl-L-cysteine;
S-(2,4-Dichlorodiphenyl)methyl-D,L-homocysteine;
S-(2,4-Difluoro-3',4'-methylenedioxydiphenyl)methyl-D,L-cysteine;
S-(2-Benzyloxydiphenyl)methyl-D,L-cysteine;
S-(3-Benzyloxydiphenyl)methyl-D,L-cysteine;
S-(2-Benzyloxy-2'-fluorodiphenyl)methyl-D,L-cysteine;
S-[2-Fluoro-2'-(2-fluorobenzyloxy)diphenyl]methyl-D,L-cysteine;
S-(2-Iododiphenyl)methyl-D,L-cystein;
S-(2-Phenyldiphenyl)methyl-D,L-cysteine;
S-(3-Fluoro-4'-*n*propyldiphenyl)methyl-D,L-cysteine;
S-(3-Fluoro-4-trifluoromethyldiphenyl)methyl-D,L-homocysteine;
S-(4,4'-Di-(dimethylamino)diphenyl)methyl-D,L-cysteine;
S-(4,4'-Di-(trifluoromethyl)diphenyl)methyl-D,L-homocysteine;
S-(4,4'-Dichlorodiphenyl)methyl-D,L-cysteine;
S-(4,4'-Dichlorodiphenyl)methyl-D,L-homocysteine;
S-(4,4'-Difluorodiphenyl)methyl-D,L-cysteine;
S-(4-Chloro-3',4'-diethyl-2-fluorodiphenyl)methyl-D,L-cysteine;
S-(4-Fluoro-2'-phenyldiphenyl)methyl-D,L-cysteine;
S-(4-Fluoro-3-trifluoromethyl-diphenyl)methyl-D,L-cysteine;
S-(4-Fluoro-3-trifluoromethyldiphenyl)methyl-D,L-homocysteine;
S-(4-Nitrodiphenyl)methyl-D,L-cysteine;
S-[α-(1-Naphthyl)-α-(4-fluorophenyl)]methyl-D,L-cysteine;
S-[α-(2-Methoxy-1-naphthyl)-α-(3-methylphenyl)]methyl-D,L-cysteine;
S-[α-(4-Methoxy-1-naphthyl)-α-(3-methylphenyl)]methyl-D,L-cysteine;
S-[α-(Indan-5-yl)-α-(2,4-difluorophenyl)]methyl-D,L-cysteine;
S-[α-(Indan-5-yl)-α-(4-fluorophenyl)]methyl-D,L-cysteine;
S-[α-(Indan-5-yl)-α-(phenyl)]methyl-D,L-cysteine;
S-[α,α-Bis(5-methyl-2-thienyl)]methyl-D,L-cysteine;
2-Amino-3-(diphenylamino)-propanoic acid;
2-Amino-5,5-di-(4-isopropylphenyl)-pentanoic acid;
S-(4-'Butyidiphenyl)methyl-D,L-homocysteine;
S-(3,4-Diethyl-2,4-difluorodiphenyl)methyl-D,L-homocysteine;
S-(3,4-Diethyl-2-fluorodiphenyl)methyl-D,L-homocysteine;
S-(3,4-Diethyl-3,4-difluorodiphenyl)methyl-D,L-homocysteine;
S-(3,4-Diethyl-3-fluorodiphenyl)methyl-D,L-homocysteine;
S-(4-'Butyldiphenyl)methyl-D,L-cysteine;
S-(4,4'-Diisopropyldiphenyl)methyl-D,L-cysteine;
S-(4,4'-Dimethyldiphenyl)methyl-D,L-cysteine;
S-(2,2',3,3',5,5',6,6'-Octamethyldiphenyl)methyl-D,L-cysteine;
S-(2,2',3,3',5,5'-Hexamethyldiphenyl)methyl-D,L-cysteine;
S-(2,2',4,4',6,6'-Hexamethyidiphenyl)methyl-D,L-cysteine;
S-(2,2',4,4'-Tetramethyidiphenyl)methyl-D,L-cysteine;
S-(2,2',5,5'-Tetramethyldiphenyl)methyl-D,L-cysteine;
S-(2,3-Diethyl-2'-fluoro-4'-methoxydiphenyl)methyl-D,L-cysteine;
S-(3,3',4,4'-Tetraethyidiphenyl)methyl-D,L-cysteine;
S-(3,4-Diethyl-2',4'-difluorodiphenyl)methyl-D,L-cysteine, methyl ester;
S-(3,4-Diethyl-2',4'-difluorodiphenyl)methyl-D,L-dimethylcysteine;
S-(3,4-Diethyl-2'-fluorodiphenyl)methyl-D,L-dimethylcysteine;
S-(3,4-Diethyl-2'-methoxydiphenyl)methyl-D,L-cysteine;
S-(3,4-Diethyl-2'-methoxydiphenyl)methyl-D,L-cysteine, methyl ester;
S-(3,4-Diethyl-2'-nitrodiphenyl)methyl-D,L-cysteine;
S-(3,4-Diethyl-2'-trifluoromethyldiphenyl)methyl-D,L-cysteine;
S-(3,4-Diethyl-3',4'-difluorodiphenyl) methyl-D,L-dimethylcysteine;
S-(3,4-Diethyl-3'-fluorodiphenyl)methyl-D,L-dimethylcysteine;
S-(3,4-Diethyl-3'-fluorodiphenyl) methyl-D,L-dimethylcysteine;

S-(3,4-Diethyl-3'-trifluoromethyldiphenyl)methyl-D,L-cysteine;
S-(3,4-Diethyl-4'-fluorodiphenyl)methyl-D,L-cysteine;
S-(3,4-Diethyl-4'-nitrodiphenyl)methyl-D,L-cysteine, methyl ester;
S-(3,4-Diethyl-4'-nitrodiphenyl)methyl-D,L-cysteine;
S-(3,4-Diethyl-4'-trifluoromethyldiphenyl)methyl-D,L-cysteine;
S-(3,4-Diethylphenyl-2',4'-difluorodiphenyl)methyl-N-methyl-D,L-cysteine;
S-(3,4-Diethylphenyl-2',4'-difluorodiphenyl)methyl-N-methyl-D,L-cysteine, methyl ester;
S-[α-(5,6,7,8-Tetrahydro-2-naphthyl)-α-(2,4-difluorophenyl)]methyl-D,L-cysteine;
S-[α-(5,6,7,8-Tetrahydro-5,5,8,8-tetramethyl-2-naphthyl)-α-(2,4-difluorophenyl)]methyl-D,L-cysteine;
S-[α-(5,6,7,8-Tetrahydronaphth-2-yl)-α-(2-nitrophenyl)]methyl-N-methyl-D,L-cysteine;
S-[α-(5,6,7,8-Tetrahydronaphth-2-yl)-α-(3-trifluoromethylphenyl)]methyl-N-methyl-D,L-cysteine and
S-[α-(5,6,7,8-Tetrahydronaphth-2-yl)-α-(4-cyanophenyl)]methyl-N-methyl-D,L-cysteine.

The pure diastereoisomers S-(R)-(3,4-Diethyl-4'-fluorodiphenyl)methyl-L-cysteine and S-(S)-(3,4-Diethyl-4'-fluorodiphenyl)methyl-L-cysteine were synthesized by coupling enantiomerically pure 3,4-diethyl-4'-fluorodiphenylthiomethanol with methyl L-N-Fmoc-O-tosylserine followed by Fmoc deprotection and ester hydrolysis. Enantiomerically pure 3,4-diethyl-4'-fluorodiphenylthiomethanols were prepared from the corresponding racemic diphenylmethanol by bromination (CH3COBr, toluene, reflux), bromine displacement with potassium thioacetate (CH$_3$COSK, DMF), chromatographic resolution of the enantiomers (Chiralcel OD column) and reductive cleavage of the thioacetate (LiAlH$_4$, ether). The experimental details are described below.

(+)-3,4-Diethyl-4'-fluorodiphenylbromomethane: Racemic 3,4-diethyl-4'-fluoro-diphenylmethanol (5.8 g, 22.4 mmol) was dissolved in 15 mL of toluene and 5 mL of acetyl bromide was added. The mixture was warmed under a nitrogen atmosphere to a gentle reflux for 3 h. The solution was concentrated, diluted with 10 mL of toluene, concentrated, diluted with 10 mL of toluene, concentrated and dried in vacuo to provide 7.2 g (100% yield) of a brown oil which was used as such in the next reaction. $^1$H NMR (CDCl$_3$) δ 7.46–6.98 (m, 7H), 6.25 (s, 1H), 2.64 (q, J=7.5 Hz, 4H), 1.21 (dt, J=2.1, 7.5 Hz, 6H).

(±)-3,4-Diethyl-4'-fluorodiphenylmethylthioacetate: (±)-3,4-Diethyl-4'-fluoro-diphenylbromo-methane (7.2 g, 22.4 mmol) in 40 mL of anhydrous DMF under argon was cooled to below 5° C. in an ice bath and 4.5 g (40 mmol) of KSCOCH$_3$ was added in one portion. The mixture was stirred at 0 to 5° C. for 30 min and was transferred into a separatory funnel using 125 mL of H$_2$O and 300 mL of ether. The aqueous phase was separated and extracted with 200 mL of ether. The combined organic fractions were washed with 2×100 mL of H$_2$O, 100 mL of brine, dried (Na$_2$SO$_4$) and concentrated to give 7 g (100% yield) of a dark orange oil after drying in vacuo. $^1$H NMR (CDCl$_3$) δ 7.34–6.95 (m, 7H), 5.88 (s, 1H), 2.61 (q, J=7.5 Hz, 4H), 2.34 (s, 3H), 1.19 (dt, J=2.9, 7.5 Hz, 6H).

Resolution of (±)-3,4-diethyl-4'-fluorodiphenylmethylthioacetate: (±)-3,4-diethyl-4'-fluoro-diphenylmethylthioacetate (5.76 g) was resolved on a 10×50 cm Chiralcele OD™ column using 100% hexanes as eluant at 35° C. A total of 2.42 g (85% recovery) of 98.3% ee compound was isolated from the first peak (retention time =11.85 minutes). The second peak (retention time=13.76 minutes) contained 2.70 g (94.4% recovery) of 97.1% ee material.

(+)-3,4-Diethyl-4'-fluorodiphenylthiomethanol: To a suspension of 190 mg (5 mmol) of LiAlH$_4$ in 25 mL of ether under argon was slowly added 1.58 g (5 mmol) of the 3,4-diethyl-4'fluorodiphenylmethylthiolacetate-(first peak to elute) dissolved in 25 mL of ether. The mixture was stirred for 30 minutes and was quenched by the careful addition of 10 mL of 5% HCl solution and subsequently 50 mL of ether. The ether layer was separated, washed with 20 mL of brine, dried (Na$_2$SO$_4$) and concentrated to provide 1.22 g (89% yield) of a colorless oil. $^1$H NMR (CDCl$_3$) δ 7.41–6.96 (m, 7H), 5.39 (d, J=4.8 Hz, 1H), 2.62 (q, J=7.5 Hz, 4H), 2.26 (d, J=4.8 Hz, 1H), 1.20 (dt, J=1.0, 7.5 Hz, 6H). $^{13}$C NMR (CDCl$_3$) δ 163.36, 160.10, 142.02, 140.83, 140.56, 139.45, 129.42, 129.32, 128.48, 127.56, 125.07, 115.40, 115.11, 46.93, 30.30, 25.53, 25.05, 15.23,15.11.

(−)-3,4-Diethyl-4'-fluorodiphenylthiomethanol was prepared in an identical manner as described for its enantiomer to provide 1.26 g (92% yield) of a colorless oil.

S-[(+)-(3,4-Diethyl-4'fluorodiphenyl)methyl]-L-cysteine: A mixture of 1.5 g (3 mmol) of methyl N-Fmoc-O-p-toluenesulfonate-L-serine, 0.82 g (3 mmol) of (+)-3,4-diethyl-4'-fluorodiphenylthiomethanol, 6 mL of acetone and 9 mL of DMF was treated with 3.25 mL (5.85 mmol) of 1.8M aqueous NaHCO$_3$. The solution was warmed with stirring to 60° C. for 4 h, then diluted with 30 mL of H$_2$O and 150 mL of EtOAc. The aqueous layer was separated and the EtOAc fraction was washed with 2×50 mL of brine, dried (NaSO$_4$) and concentrated. Chromatography over SiO$_2$ (Biotage 40M column) using EtOAc/hexanes (18/82) as eluant provided an oil. $^1$H NMR (CDCl$_3$) δ 7.78–6.94 (m, 15H), 5.56 (d, J=7.8 Hz, 1H), 5.14 (s, 1H), 4.58 (s, 1H), 4.39 (d, J=6.7 Hz, 2H), 4.23 (t, J=6.7 Hz, 1H), 3.74 (s, 3H), 2.84–2.77 (m, 2H), 2.65–2.56 (m, 4H), 1.25–1.15 (m, 6H).

The oil was treated with 5 mL of piperidine, stirred under argon for 18 h, and concentrated to a solid. The solid was suspended in 20 mL of MeOH and 6 mL of 1.0M aqueous NaOH was added. The reaction stirred for 3 h and was concentrated to dryness, diluted with 30 mL of H$_2$O and 30 mL of ether. The aqueous layer was separated, washed with 2×20 mL of ether and neutralized to pH 6 with glacial acetic acid. The white precipitate was filtered, washed with 2×10 mL of H$_2$O and dried in vacuo to provide 270 mg (25% yield) of the desired product as a white powder. $[α]^{20}_D$=+1.14° (c=0.7, 0.2N NaOH). $^1$H NMR (dmso-d$_6$) δ 7.49–7.01 (m, 7H), 5.39 (s, 1H), 3.30 (dd, J=4.3, 8.3, 1H), 2.79–2.74 (m, 1H), 2.58–2.50 (m, 5H), 1.13 (t, J=7.5 Hz, 6H).

S-[(−)-(3,4-Diethyl-4'fluorodiphenyl)methyl]-L-cysteine was prepared in an analogous manner and in similar yield as described above for its diastereoisomer by coupling (−)-3,4-diethyl-4'-fluorodiphenylthiomethanol with N-Fmoc-O-p-toluenesulfonate-L-serine. $[α]^{20}_D$−0.60 (c=1.17, 0.2N NaOH).

| Summary of Exemplified Compounds | | | | | | | |
|---|---|---|---|---|---|---|---|
| X | Ar$^1$ | Ar$^2$ | R$^3$ | Y | R$^4$ | R$^5$ | R$^6$ |
| S | 1-naphthyl | 4-fluorophenyl | H | CH$_2$ | H | H | H |
| S | 2-(2-fluorobenzyloxy)phenyl | 2-fluorophenyl | H | CH$_2$ | H | H | H |
| S | 2-(4-methoxybenzyloxy)phenyl | phenyl | H | CH$_2$ | H | H | H |
| S | 2,3,5,6-tetramethylphenyl | 2,3,5,6-tetramethylphenyl | H | CH$_2$ | H | H | H |
| S | 2,3,5-trimethylphenyl | 2,3,5-trimethylphenyl | H | CH$_2$ | H | H | H |
| S | 2,3-diethylphenyl | 2-fluoro-4-methoxyphenyl | H | CH$_2$ | H | H | H |
| S | 2,4,6-trimethylphenyl | 2,4,6-trimethylphenyl | H | CH$_2$ | H | H | H |
| S | 2,4-dichlorophenyl | phenyl | H | (CH$_2$)$_2$ | H | H | H |
| S | 2,4-dichlorophenyl | phenyl | H | CH$_2$ | H | H | H |
| S | 2,4-dimethylphenyl | 2,4-dimethylphenyl | H | CH$_2$ | H | H | H |
| S | 2,5-dimethylphenyl | 2,5-dimethylphenyl | H | CH$_2$ | H | H | H |
| S | 2-benzyloxyphenyl | 2-fluorophenyl | H | CH$_2$ | H | H | H |
| S | 2-benzyloxyphenyl | phenyl | H | CH$_2$ | H | H | H |
| S | 2-iodophenyl | phenyl | H | CH$_2$ | H | H | H |
| S | 2-methoxy-1-naphthyl | 3-methylphenyl | H | CH$_2$ | H | H | H |
| S | 2-phenylphenyl | 4-fluorophenyl | H | CH$_2$ | H | H | H |
| S | 2-phenylphenyl | phenyl | | | | | |
| S | 3,4-diethylphenyl | 2,4-difluorophenyl | H | (CH$_2$)$_2$ | H | H | H |
| S | 3,4-diethylphenyl | 2,4-difluorophenyl | H | CH$_2$ | H | H | H |
| S | 3,4-diethylphenyl | 2,4-difluorophenyl | H | CH$_2$ | H | H | Me |
| S | 3,4-diethylphenyl | 2,4-difluorophenyl | H | CH$_2$ | H | H | COCH$_3$ |
| S | 3,4-diethylphenyl | 2,4-difluorophenyl | H | CH$_2$ | Me | H | Me |
| S | 3,4-diethylphenyl | 2,4-difluorophenyl | H | CH$_2$ | Me | H | H |
| S | 3,4-diethylphenyl | 2,4-difluorophenyl | H | CMe$_2$ | H | H | H |
| S | 3,4-diethylphenyl | 2,4-difluorophenyl | Me | H | H | H | H |
| S | 3,4-diethylphenyl | 2,6-difluorophenyl | H | CH$_2$ | H | H | H |
| S | 3,4-diethylphenyl | 2-chloro-4-fluorophenyl | H | CH$_2$ | H | H | H |
| S | 3,4-diethylphenyl | 2-fluoro-4-methoxy phenyl | H | CH$_2$ | H | H | H |
| S | 3,4-diethylphenyl | 2-fluoro-4-trifluoromethylphenyl | H | CH$_2$ | H | H | H |
| S | 3,4-diethylphenyl | 2-fluorophenyl | H | (CH$_2$)$_2$ | H | H | H |
| S | 3,4-diethylphenyl | 2-fluorophenyl | H | CH$_2$ | H | H | H |
| S | 3,4-diethylphenyl | 2-fluorophenyl | H | CMe$_2$ | H | H | H |
| S | 3,4-diethylphenyl | 2-methoxyphenyl | H | CH$_2$ | H | H | Me |
| S | 3,4-diethylphenyl | 2-methoxyphenyl | H | CH$_2$ | H | H | H |
| S | 3,4-diethylphenyl | 2-nitrophenyl | H | CH$_2$ | H | H | H |
| S | 3,4-diethylphenyl | 2-trifluoromethylphenyl | H | CH$_2$ | H | H | H |
| S | 3,4-diethylphenyl | 3,4-diethylphenyl | H | CH$_2$ | H | H | H |
| S | 3,4-diethylphenyl | 3,4-difluorophenyl | H | (CH$_2$)$_2$ | H | H | H |
| S | 3,4-diethylphenyl | 3,4-difluorophenyl | H | CH$_2$ | H | H | H |
| S | 3,4-diethylphenyl | 3,4-difluorophenyl | H | CMe$_2$ | H | H | H |
| S | 3,4-diethylphenyl | 3,5-difluorophenyl | H | CH$_2$ | H | H | H |
| S | 3,4-diethylphenyl | 3-fluorophenyl | H | (CH$_2$)$_2$ | H | H | H |
| S | 3,4-diethylphenyl | 3-fluorophenyl | H | CH$_2$ | H | H | H |
| S | 3,4-diethylphenyl | 3-fluorophenyl | H | CMe$_2$ | H | H | H |
| S | 3,4-diethylphenyl | 3-trifluoromethylphenyl | H | CH$_2$ | H | H | H |
| S | 3,4-diethylphenyl | 4-chloro-2-fluorophenyl | H | CH$_2$ | H | H | H |
| S | 3,4-diethylphenyl | 4-fluorophenyl | H | CH$_2$ | H | H | H |
| S | 3,4-diethylphenyl | 4-fluorophenyl | H | CMe$_2$ | H | H | H |
| S | 3,4-diethylphenyl | 4-nitrophenyl | H | CH$_2$ | H | H | Me |
| S | 3,4-diethylphenyl | 4-nitrophenyl | H | CH$_2$ | H | H | H |
| S | 3,4-diethylphenyl | 4-trifluoromethylphenyl | H | CH$_2$ | H | H | H |
| S | 3,4-diethylphenyl | phenyl | H | CH$_2$ | H | H | H |
| S | 3,4-dimethylphenyl | 3,4-dimethylphenyl | H | CH$_2$ | H | H | H |
| S | 3,4-methylene-dioxyphenyl | 2,4-difluorophenyl | H | CH$_2$ | H | H | H |
| S | 3-benzyloxyphenyl | phenyl | H | CH$_2$ | H | H | H |
| S | 3-fluoro-4-trifluoromethyl-phenyl | phenyl | H | (CH$_2$)$_2$ | H | H | H |
| S | 4-chlorophenyl | 4-chlorophenyl | H | (CH$_2$)$_2$ | H | H | H |
| S | 4-chlorophenyl | 4-chlorophenyl | H | CH$_2$ | H | H | H |
| S | 4-dimethylaminophenyl | 4-dimethylaminophenyl | H | CH$_2$ | H | H | H |
| S | 4-ethylphenyl | 2,4-difluorophenyl | H | CH$_2$ | H | H | H |
| S | 4-ethylphenyl | 3-fluorophenyl | H | CH$_2$ | H | H | H |
| S | 4-ethylphenyl | 4-fluorophenyl | H | CH$_2$ | H | H | H |
| S | 4-ethylphenyl | phenyl | H | CH$_2$ | H | H | H |
| S | 4-fluoro-3-trifluoromethyl-phenyl | phenyl | H | (CH$_2$)$_2$ | H | H | H |
| S | 4-fluoro-3-trifluoromethyl-phenyl | phenyl | H | CH$_2$ | H | H | H |
| S | 4-fluorophenyl | 4-fluorophenyl | H | CH$_2$ | H | H | H |
| S | 4-isopropylphenyl | 4-isopropylphenyl | H | CH$_2$ | H | H | H |
| S | 4-methoxy-1-naphthyl | 3-methylphenyl | H | CH$_2$ | H | H | H |
| S | 4-methylphenyl | 4-methylphenyl | H | CH$_2$ | H | H | H |
| S | 4-nitrophenyl | phenyl | H | CH$_2$ | H | H | H |
| S | 4-n-propylphenyl | 2,4-difluorophenyl | H | CH$_2$ | H | H | H |

-continued

Summary of Exemplified Compounds

| X | Ar$^1$ | Ar$^2$ | R$^3$ | Y | R$^4$ | R$^5$ | R$^6$ |
|---|---|---|---|---|---|---|---|
| S | 4-n-propylphenyl | 3-fluorophenyl | H | CH$_2$ | H | H | H |
| S | 4-t-butylphenyl | phenyl | H | CH$_2$ | H | H | H |
| S | 4-tert-butylphenyl | phenyl | H | (CH$_2$)$_2$ | H | H | H |
| S | 4-trifluoromethylphenyl | 4-trifluoromethylphenyl | H | (CH$_2$)$_2$ | H | H | H |
| S | 5,6,7,8-tetrahydro-2-naphthyl | 2,4-difluorophenyl | H | CH$_2$ | H | H | H |
| S | 5,6,7,8-tetrahydro-5,5,8,8-tetramethyl-naphth-2-yl | 2,4-difluorophenyl | H | CH$_2$ | H | H | H |
| S | 5,6,7,8-tetrahydro-naphth-2-yl | 2,4-difluorophenyl | H | CH$_2$ | H | H | H |
| S | 5,6,7,8-tetrahydro-naphth-2-yl | 2-nitrophenyl | H | CH$_2$ | Me | H | H |
| S | 5,6,7,8-tetrahydro-naphth-2-yl | 3,4-trifluoromethylphenyl | H | CH$_2$ | Me | H | H |
| S | 5,8,7,8-tetrahydro-naphth-2-yl | 4-cyanophenyl | H | CH$_2$ | Me | H | H |
| S | 5-methyl-2-thienyl | 5-methyl-2-thienyl | H | CH$_2$ | H | H | H |
| S | Indan-5-yl | 2,4-difluorophenyl | H | CH$_2$ | H | H | H |
| S | Indan-5-yl | 2,4-difluorophenyl | H | CH$_2$ | H | H | H |
| S | Indan-5-yl | 4-fluorophenyl | H | CH$_2$ | H | H | H |
| S | Indan-5-yl | phenyl | H | CH$_2$ | H | H | H |
| NH | phenyl | phenyl | H | CH$_2$ | H | H | H |
| CH$_2$ | 4-isopropylphenyl | 4-isopropylphenyl | H | CH$_2$ | H | H | H |

EXAMPLE 4

Assay of Transport via GlyT-1 or GlyT-2 Transporters

This example illustrates a method for the measurement of glycine uptake by transfected cultured cells.

Cells transiently transfected with GlyT-1C (see Kim, et al., *Molecular Pharmacology*, 45, 1994:608–617) and human GlyT-2 (the homolog of the rat GlyT-2 described by Liu et al., *J. Biological Chemistry*, 268, 1993.22802–22808) were washed three times with HEPES buffered saline (HBS). The cells were then incubated 10 minutes at 37° C., after which a solution containing 50 nM [$^3$H]glycine (17.5 Ci/mmol) and either (a) no potential competitor, (b) 10 nM nonradioactive glycine or (c) a concentration of a candidate drug. A range of concentrations of the candidate drug was used to generate data for calculating the concentration resulting in 50% of the effect (e.g., the IC$_{50}$'s which are the concentration of drug inhibiting glycine uptake by 50%). The cells were then incubated another 10 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the same cells contacted and not contacted by the candidate agent, and between cells having GlyT-1 activity versus cells having GlyT-2 activity, depending on the assay being conducted.

All exemplified compounds of the invention were tested for inhibition of glycine transport and displayed a pIC$_{50}$ in the range of from about 4 to about 8.5. Preferred compounds of the invention showed selectivity for the inhibition of glycine transport via GlyT-2 versus GlyT-1; representative (but not limiting) examples of these being S-(3,4-Diethyl-2',4'-difluorodiphenyl)methyl-D,L-cysteine, S-(4-Fluoro-2'-phenyldiphenyl)methyl-D,L-cysteine, S-(4,4'-Dimethyldiphenyl)methyl-D,L-cysteine, S-(3,4-Diethyl-2'-fluorodiphenyl)methyl-D,L-dimethylcysteine, S-(3,4-Diethyl-4'-nitrodiphenyl)methyl-D,L-cysteine, S-[α-(5,6,7,8-Tetrahydronaphth-2-yl)-α-(2,4-difluorophenyl)]methyl-D,L-cysteine and S-[α,α-Bis(5-methyl-2-thienyl)]methyl-D,L-cysteine.

Representative (but not limiting) examples of compounds exhibiting mixed GlyT-1/GlyT-2 activity include S-(4'-Butyidiphenyl)methyl-D,L-homocysteine; S-(2,4-Difluoro-4'-"propyldiphenyl)methyl-D,L-cysteine; S-(3,4-Diethyl-4-fluorodiphenyl)methyl-D,L-dimethylcysteine; S-(3,4-Diethyl-3'-fluorodiphenyl)methyl-D,L-cysteine and S-(3,4-Diethyl-3'-trifluoromethyidiphenyl)methyl-D,L-cysteine.

EXAMPLE 5

Assay of Transport Via the GAT-1 Transporter

This example illustrates a method for the measurement of gamma-amino butyric acid (GABA) uptake by transfected cultured cells.

Cells transiently transfected with GAT-1 (Nelson, H., Mandiyan, S., and Nelson N. *FEBS Lett.* 269 1990:181–184) and plated in 24-well tissue culture plates were washed twice with HEPES buffered saline (HBS). 200 μl of HBS was added to each well, after which 25 μl of competing drug or vehicle was added and the cells incubated for 15 minutes at room temperature. A range of concentrations of the candidate drug was used to generate data for calculating the concentration resulting in 50% of the maximum effect (i.e. the IC50 value, which is the concentration of drug inhibiting GABA uptake by 50%). 25 μl of a 25 nM solution of [3H]GABA (89 Ci/mmol) was then added. Separate wells were treated with 25 μl of 25 nM [3H]GABA, with or without cold GABA at 10 μM. The cells were then incubated another 15 minutes at room temperature, after which the supernatant was aspirated and the cells washed twice with ice-cold HBS. The cells were solubilized in scintillant, shaken for 30 minutes, and the radioactivity in the cells was counted using a scintillation counter. Exemplified compounds of the invention were tested for inhibition of GABA transport via GAT-1 and certain of these displayed a pIC$_{50}$ in the range of from about 4 to about 7; representative (but not limiting) examples of these being S-[2-(4-Phenyl) diphenyl]methyl-L-cysteine, S-[2-(3,4-Diethyl-2'-nitro)-diphenyl]methyl-L-cysteine and S-[2-(2,4-Difluoro-4'-ethyl)diphenyl]methyl-L-cysteine.

We claim:
1. A compound selected from the group consisting of a compound of the formula;

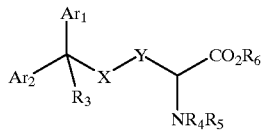

wherein;
- $Ar^1$ and $Ar^2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NRR'$, NRR', $CO_2R$ (where R and R' are independently selected from the group consisting of H and alkyl) and a second aryl group, which may be substituted as above;
- wherein any cycloalkyl or aryl substituent is linked to $Ar^1$ or $Ar^2$ by a bridging element which may be a single bond, a vinylene group, an ethynylene group, a Z group, a $-Z-(CH_2)_n-$ group, a $-(CH_2)_n-Z-$ group, or a $-Z-(CH_2)_n-Z-$ group, where Z represents an O atom, a S atom, an NH group or an N-alkyl group, and n is an integer from 1 to 4;
- wherein $Ar^1$ and $Ar^2$ may be attached to the central atom to which they are connected by a single bond, an alkylene, alkenylene or alkynylene group;
- wherein $Ar^1$ and $Ar^2$ may be attached to the central atom to which they are connected by a single bond, an alkylene, alkenylene or alkynylene group;
- $R^3$ is selected from the group consisting of H and aryl, which may be substituted as for $Ar^1$;
- $R^4$ and $R^5$ are independently selected from the group consisting of H, alkyl, alkanoyl, benzoyl and benzyl;
- $R^6$ is selected from the group consisting of H and an alkyl group having up to 20 carbon atoms,
- X is selected from the group consisting of S, SO, $SO_2$, NR and CRR', where R and R' are independently selected from the group consisting of H, alkyl, aryl and aralkyl;
- Y is a methylene or ethylene linking element, optionally substituted with one or more substituents independently selected from the group consisting of alkyl and phenyl;
- with the following provisos:
  - when $Ar^1$ and $Ar^2$ are phenyl rings, $R^3$ is H or a phenyl ring, and $R^4$–$R^6$ are each H at least one of groups $Ar^1$ and $Ar^2$ must be substituted,
  - when X=S and $R^4$ and $R^5$ are each H, and $R^6$ is H or alkyl:
    (i) $Ar^2$ cannot be unsubstituted phenyl when $Ar^1$ is 4-monosubstituted phenyl,
    (ii) $Ar^1$ and $Ar^2$ cannot both be 4-methoxyphenyl when $R^3$ is H or unsubstituted phenyl,
    (iii) $Ar^1$, $Ar^2$ and $R^3$ cannot all be 3-fluorophenyl or 4-methoxyphenyl,
    (iv) $Ar^1$ and $Ar^2$ cannot both be 4-hydroxymethylphenyl when $R^3$ is unsubstituted phenyl,
and a stereoisomer, salt, solvate and hydrate thereof.

2. A compound according to claim 1 wherein X is S.
3. A compound according to claim 1 or claim 2 wherein $R^3$ is H.
4. A compound according to claim 1 wherein $Ar^1$ and $Ar^2$ are substituted phenyl rings, the substituents being independently selected from the group consisting of alkyl, alkoxy, halo, $NO_2$, Ph and $CF_3$.
5. A compound according to claim 4 wherein $Ar^1$ is an alkyl-substituted phenyl group.
6. A compound according to claim 5 wherein $Ar^1$ is a 3,4-diethylphenyl group.
7. A compound according to claim 5 wherein $Ar^1$ is a 5,6,7,8-Tetrahydronaphth-2-yl group.
8. A compound according to claim 4 wherein $Ar^2$ is a halo-substituted phenyl group.
9. A compound according to claim 7 wherein $Ar^2$ is a fluoro-substituted phenyl group.
10. A compound according to claim 8 wherein $Ar^2$ is a 2,4-difluorophenyl group.
11. A compound according to claim 9 wherein $R^4$, $R^5$, $R^6$, $R^7$ and $R^8$ are each H.
12. A compound selected from the group consisting of:
S-(2,4-Dichlorodiphenyl)methyl-D,L-cysteine;
S-(2,4-Dichlorodiphenyl)methyl-D,L-homocysteine;
S-(2,4-Difluoro-3',4'-methylenedioxydiphenyl)methyl-D,L-cysteine;
S-(2-Benzyloxydiphenyl)methyl-D,L-cysteine;
S-(3-Benzyloxydiphenyl)methyl-D,L-cysteine;
S-(2-Benzyloxy-2'-fluorodiphenyl)methyl-D,L-cysteine;
S-[2-Fluoro-2'-(2-fluorobenzyloxy)diphenyl]methyl-D,L-cysteine;
S-(2-Iododiphenyl)methyl-D,L-cysteine;
S-(2-Phenyldiphenyl)methyl-D,L-cysteine;
S-(3-Fluoro-4'-"propyldiphenyl)methyl-D,L-cysteine;
S-(3-Fluoro-4-trifluoromethyldiphenyl)methyl-D,L-homocysteine;
S-(4,4'-Di-(dimethylamino)diphenyl)methyl-D,L-cysteine;
S-(4,4'-Di-(trifluoromethyl)diphenyl)methyl-D,L-homocysteine;
S-(4,4'-Dichlorodiphenyl)methyl-D,L-cysteine;
S-(4,4'-Dichlorodiphenyl)methyl-D,L-homocysteine;
S-(4,4'-Difluorodiphenyl)methyl-D,L-cysteine;
S-(4-Chloro-3',4'-diethyl-2-fluorodiphenyl)methyl-D,L-cysteine;
S-(4-Fluoro-2'-phenyldiphenyl)methyl-D,L-cysteine;
S-(4-Fluoro-3-trifluoromethyl-diphenyl)methyl-D,L-cysteine;
S-(4-Fluoro-3-trifluoromethyldiphenyl)methyl-D,L-homocysteine;
S-(4-Nitrodiphenyl)methyl-D,L-cysteine;
S-[α-(1-Naphthyl)-α-(4-fluorophenyl)]methyl-D,L-cysteine;
S-[α-(2-(4-Methoxybenzyloxy)phenyl)-α-phenyl]methyl-D,L-cysteine;
S-[α-(2-Methoxy-1-naphthyl)-α-(3-methylphenyl)]methyl-D,L-cysteine;
S-[α-(4-Methoxy-1-naphthyl)-α-(3-methylphenyl)]methyl-D,L-cysteine;
S-[α-(Indan-5-yl)-α-(2,4-difluorophenyl)]methyl-D,L-cysteine;
S-[α-(Indan-5-yl)-α-(4-fluorophenyl)]methyl-D,L-cysteine;
S-[α-(Indan-5-yl)-α-(phenyl)]methyl-D,L-cysteine;
S-[α,α-Bis(5-methyl-2-thienyl)]methyl-D,L-cysteine;
2-Amino-3-(diphenylamino)-propanoic acid;
2-Amino-5,5-di-(4-isopropylphenyl)-pentanoic acid;
S-(4-'Butyldiphenyl)methyl-D,L-homocysteine;
S-(3,4-Diethyl-2,4-difluorodiphenyl)methyl-D,L-homocysteine;
S-(3,4-Diethyl-2-fluorodiphenyl)methyl-D,L-homocysteine;
S-(3,4-Diethyl-3,4-difluorodiphenyl)methyl-D,L-homocysteine;

S-(3,4-Diethyl-3-fluorodiphenyl)methyl-D,L-homocysteine;
S-(4-'Butyldiphenyl)methyl-D,L-cysteine;
S-(4,4'-Diisopropyldiphenyl)methyl-D,L-cysteine;
S-(4,4'-Dimethyldiphenyl)methyl-D,L-cysteine;
S-(2,2',3,3',5,5',6,6'-Octamethyldiphenyl)methyl-D,L-cysteine;
S-(2,2',3,3',5,5'-Hexamethyldiphenyl)methyl-D,L-cysteine;
S-(2,2',4,4',6,6'-Hexamethyldiphenyl)methyl-D,L-cysteine;
S-(2,2',4,4'-Tetramethyldiphenyl)methyl-D,L-cysteine;
S-(2,2',5,5'-Tetramethyldiphenyl)methyl-D,L-cysteine;
S-(2,3-Diethyl-2'-fluoro-4'-methoxydiphenyl)methyl-D,L-cysteine;
S-(3,3',4,4'-Tetraethyldiphenyl)methyl-D,L-cysteine;
S-(3,4-Diethyl-2',4'-difluorodiphenyl)methyl-D,L-cysteine, methyl ester;
S-(3,4-Diethyl-2',4'-difluorodiphenyl)methyl-D,L-dimethylcysteine;
S-(3,4-Diethyl-2'-fluorodiphenyl)methyl-D,L-dimethylcysteine;
S-(3,4-Diethyl-2'-methoxydiphenyl)methyl-D,L-cysteine;
S-(3,4-Diethyl-2'-methoxydiphenyl)methyl-D,L-cysteine, methyl ester;
S-(3,4-Diethyl-2'-nitrodiphenyl)methyl-D,L-cysteine;
S-(3,4-Diethyl-2'-trifluoromethyldiphenyl)methyl-D,L-cysteine;
S-(3,4-Diethyl-3',4'-difluorodiphenyl)methyl-D,L-dimethylcysteine;
S-(3,4-Diethyl-3'-fluorodiphenyl)methyl-D,L-dimethylcysteine;
S-(3,4-Diethyl-3'-fluorodiphenyl)methyl-D,L-dimethylcysteine;
S-(3,4-Diethyl-3'-trifluoromethyldiphenyl)methyl-D,L-cysteine;
S-(3,4-Diethyl-4'-fluorodiphenyl)methyl-D,L-cysteine;
S-(3,4-Diethyl-4'-nitrodiphenyl)methyl-D,L-cysteine;
S-(3,4-Diethyl-4'-nitrodiphenyl)methyl-D,L-cysteine, methyl ester;
S-(3,4-Diethyl-4'-nitrodiphenyl)methyl-D,L-cysteine;
S-(3,4-Diethyl-4'-trifluoromethyldiphenyl)methyl-D,L-cysteine;
S-(3,4-Diethylphenyl-2',4'-difluorodiphenyl)methyl-N-methyl-D,L-cysteine;
S-(3,4-Diethylphenyl-2',4'-difluorodiphenyl)methyl-N-methyl-D,L-cysteine, methyl ester
S-[α-(5,6,7,8-Tetrahydro-5,5,8,8-tetramethyl-2-naphthyl)-α-(2,4-difluorophenyl)]methyl-D,L-cysteine;
S-[α-(5,6,7,8-Tetrahydronaphth-2-yl)-α-(2,4-difluorophenyl)]methyl-D,L-cysteine;
S-[α-(5,6,7,8-Tetrahydronaphth-2-yl)-α-(2-nitrophenyl)]methyl-N-methyl-D,L-cysteine;
S-[α-(5,6,7,8-Tetrahydronaphth-2-yl)-α-(3-trifluoromethylphenyl)]methyl-N-methyl-D,L-cysteine; and
S-[α-(5,6,7,8-Tetrahydronaphth-2-yl)-α-(4-cyanophenyl)]methyl-N-methyl-D,L-cysteine.

13. A pharmaceutical composition comprising a therapeutically effective amount of a compound of the formula;

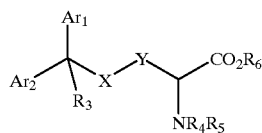

wherein;
Ar$^1$ and Ar$^2$ are independently selected aryl groups, optionally substituted with substituents selected from the group consisting of alkyl, cycloalkyl, alkoxy, alkanoyl, aralkyl, aralkyloxy, halo, NO$_2$, Ph, CF$_3$, CN, OH, methylenedioxy, ethylenedioxy, SO$_2$NRR', NRR', CO$_2$R (where R and R' are independently selected from the group consisting of H and alkyl) and a second aryl group, which may be substituted as above;
wherein any cycloalkyl or aryl substituent is linked to Ar$^1$ or Ar$^2$ by a bridging element which may be a single bond, a vinylene group, an ethynylene group, a Z group, a —Z—(CH$_2$)$_n$— group, a —(CH$_2$)$_n$—Z— group, or a —Z—(CH$_2$)$_n$—Z— group, where Z represents an O atom, a S atom, an NH group or an N-alkyl group, and n is an integer from 1 to 4;
wherein Ar$^1$ and Ar$^2$ may be attached to the central atom to which they are connected by a single bond, an alkylene, alkenylene or alkynylene group;
wherein Ar$^1$ and Ar$^2$ may be attached to the central atom to which they are connected by a single bond, an alkylene, alkenylene or alkynylene group;
R$^3$ is selected from the group consisting of H and aryl which may be substituted as for Ar$^1$;
R$^4$ and R$^5$ are independently selected from the group consisting of H, alkyl, alkanoyl, benzoyl and benzyl;
R$^6$ is selected from the group consisting of H and an alkyl group having up to 20 carbon atoms,
X is selected from the group consisting of S, SO, SO$_2$, NR and CRR', where R and R' are independently selected from the group consisting of H, alkyl, aryl and aralkyl;
Y is a methylene or ethylene linking element, optionally substituted with one or more substituents independently selected from the group consisting of alkyl and phenyl;
with the following provisos;
when Ar$^1$ and Ar$^2$ are phenyl rings R$^3$ is H or a phenyl ring, and R$^4$–R$^6$ are each H at least one of groups Ar$^1$ and Ar$^2$ must be substituted,
when X=S and R$^4$–R$^6$ are each H;
(i) Ar$^1$ cannot be unsubstituted phenyl when Ar$^1$ is 4-monosubstituted phenyl,
(ii) Ar$^1$ and Ar$^2$ cannot both be 4-methoxyphenyl when R$^3$ is H or unsubstituted phenyl,
(iii) Ar$^1$, Ar$^2$ and R$^3$ cannot all be 3-fluorophenyl or 4-methoxyphenyl,
(iv) Ar$^1$ and Ar$^2$ cannot both be 4-hydroxymethylphenyl when R$^3$ is unsubstituted phenyl,
and a stereoisomer, salt, solvate and hydrate thereof; and a pharmaceutically acceptable carrier.

14. A compound according to claim 1 wherein Ar$^1$ and Ar$^2$ are substituted phenyl rings, the substituents comprising one or more alkyl, halo, NO$_2$, Ph or CF$_3$ groups.

15. A composition according to claim 13, wherein in the compound X is S.

16. A composition according to claim 13 or claim 24, wherein in the compound R$^3$ is H.

17. A composition according to claim 13, wherein in the compound Ar$^1$ and Ar$^2$ are substituted phenyl rings, the substituents being independently selected from the group consisting of alkyl, alkoxy, halo, NO$_2$, Ph and CF$_3$.

18. A composition according to claim 17, wherein in the compound Ar$^1$ is an alkyl-substituted phenyl group.

19. A composition according to claim 18, wherein in the compound Ar$^1$ is a 3,4-diethylphenyl group.

20. A composition according to claim 18, wherein in the compound Ar$^1$ is a 5,6,7,8-Tetrahydronaphth-2-yl group.

21. A composition according to claim 17, wherein in the compound Ar$^2$ is a halo-substituted phenyl group.

22. A composition according to claim 20, wherein in the compound Ar² is a fluoro-substituted phenyl group.

23. A composition according to claim 22, wherein in the compound Ar² is a 2,4-difluorophenyl group.

24. A composition according to claim 23, wherein in the compound R⁴, R⁵ and R⁶ are each H.

25. A composition according to claim 13, wherein in the compound is selected from the group consisting of;
S-(2,4-Dichlorodiphenyl)methyl-D,L-cysteine;
S-(2,4-Dichlorodiphenyl)methyl-D,L-homocysteine;
S-(2,4-Difluoro-3',4'-methylenedioxydiphenyl)methyl-D,L-cysteine;
S-(2-Benzyloxydiphenyl)methyl-D,L-cysteine;
S-(3-Benzyloxydiphenyl)methyl-D,L-cysteine;
S-(2-Benzyloxy-2'-fluorodiphenyl)methyl-D,L-cysteine;
S-[2-Fluoro-2'-(2-fluorobenzyloxy)diphenyl]methyl-D,L-cysteine;
S-(2-Iododiphenyl)methyl-D,L-cysteine;
S-(2-Phenyldiphenyl)methyl-D,L-cysteine;
S-(3-Fluoro-4-″-npropyldiphenyl)methyl-D,L-cysteine;
S-(3-Fluoro-4-trifluoromethyldiphenyl)methyl-D,L-homocysteine;
S-(4,4'-Di-(dimethylamino)diphenyl)methyl-D,L-cysteine;
S-(4,4'-Di-(trifluoromethyl)diphenyl)methyl-D,L-homocysteine;
S-(4,4'-Dichlorodiphenyl)methyl-D,L-cysteine;
S-(4,4'-Dichlorodiphenyl)methyl-D,L-homocysteine;
S-(4,4'-Difluorodiphenyl)methyl-D,L-cysteine;
S-(4-Chloro-3',4'-diethyl-2-fluorodiphenyl)methyl-D,L-cysteine;
S-(4-Fluoro-2'-phenyldiphenyl)methyl-D,L-cysteine;
S-(4-Fluoro-3-trifluoromethyl-diphenyl)methyl-D,L-cysteine;
S-(4-Fluoro-3-trifluoromethyldiphenyl)methyl-D,L-homocysteine;
S-(4-Nitrodiphenyl)methyl-D,L-cysteine;
S-[α-(1-Naphthyl)-α-(4-fluorophenyl)]methyl-D,L-cysteine;
S-[α-(2-(4-Methoxybenzyloxy)phenyl)-α-phenyl]methyl-D,L-cysteine;
S-[α-(2-Methoxy-1-naphthyl)-α-(3-methylphenyl)]methyl-D,L-cysteine;
S-[α-(4-Methoxy-1-naphthyl)-α-(3-methylphenyl)]methyl-D,L-cysteine;
S-[α-(Indan-5-yl)-α-(2,4-difluorophenyl)]methyl-D,L-cysteine;
S-[α-(Indan-5-yl)-α-(4-fluorophenyl)]methyl-D,L-cysteine;
S-[α-(Indan-5-yl)-α-(phenyl)]methyl-D,L-cysteine;
S-[α,α-Bis(5-methyl-2-thienyl)]methyl-D,L-cysteine;
2-Amino-3-(diphenylamino)-propanoic acid;
2-Amino-5,5-di-(4-isopropylphenyl)-pentanoic acid;
S-(4-ᵗButyldiphenyl)methyl-D,L-homocysteine;
S-(3,4-Diethyl-2,4-difluorodiphenyl)methyl-D,L-homocysteine;
S-(3,4-Diethyl-2-fluorodiphenyl)methyl-D,L-homocysteine;
S-(3,4-Diethyl-3,4-difluorodiphenyl)methyl-D,L-homocysteine;
S-(3,4-Diethyl-3-fluorodiphenyl)methyl-D,L-homocysteine;
S-(4-ᵗButyldiphenyl)methyl-D,L-cysteine;
S-(4,4'-Diisopropyldiphenyl)methyl-D,L-cysteine;
S-(4,4'-Dimethyldiphenyl)methyl-D,L-cysteine;
S-(2,2',3,3',5,5',6,6'-Octamethyldiphenyl)methyl-D,L-cysteine;
S-(2,2',3,3',5,5'-Hexamethyldiphenyl)methyl-D,L-cysteine;
S-(2,2',4,4',6,6'-Hexamethyldiphenyl)methyl-D,L-cysteine;
S-(2,2',4,4'-Tetramethyldiphenyl)methyl-D,L-cysteine;
S-(2,2',5,5'-Tetramethyldiphenyl)methyl-D,L-cysteine;
S-(2,3-Diethyl-2'-fluoro-4'-methoxydiphenyl)methyl-D,L-cysteine;
S-(3,3',4,4'-Tetraethyldiphenyl)methyl-D,L-cysteine;
S-(3,4-Diethyl-2',4'-difluorodiphenyl)methyl-D,L-cysteine, methyl ester;
S-(3,4-Diethyl-2',4'-difluorodiphenyl)methyl-D,L-dimethylcysteine;
S-(3,4-Diethyl-2'-fluorodiphenyl)methyl-D,L-dimethylcysteine;
S-(3,4-Diethyl-2'-methoxydiphenyl)methyl-D,L-cysteine;
S-(3,4-Diethyl-2'-methoxydiphenyl)methyl-D,L-cysteine, methyl ester;
S-(3,4-Diethyl-2'-nitrodiphenyl)methyl-D,L-cysteine;
S-(3,4-Diethyl-2'-trifluoromethyldiphenyl)methyl-D,L-cysteine;
S-(3,4-Diethyl-3',4'-difluorodiphenyl)methyl-D,L-dimethylcysteine;
S-(3,4-Diethyl-3'-fluorodiphenyl)methyl-D,L-dimethylcysteine;
S-(3,4-Diethyl-3'-fluorodiphenyl)methyl-D,L-dimethylcysteine;
S-(3,4-Diethyl-3'-trifluoromethyldiphenyl)methyl-D,L-cysteine;
S-(3,4-Diethyl-4'-fluorodiphenyl)methyl-D,L-cysteine;
S-(3,4-Diethyl-4'-nitrodiphenyl)methyl-D,L-cysteine, methyl ester;
S-(3,4-Diethyl-4'-nitrodiphenyl)methyl-D,L-cysteine;
S-(3,4-Diethyl-4'-trifluoromethyldiphenyl)methyl-D,L-cysteine;
S-(3,4-Diethylphenyl-2',4'-difluorodiphenyl)methyl-N-methyl-D,L-cysteine;
S-(3,4-Diethylphenyl-2',4'-difluorodiphenyl)methyl-N-methyl-D,L-cysteine, methyl ester;
S-[α-(5,6,7,8-Tetrahydro-5,5,8,8-tetramethyl-2-naphthyl)-α-(2,4-difluorophenyl)]methyl-D,L-cysteine;
S-[α-(5,6,7,8-Tetrahydronaphth-2-yl)-α-(2,4-difluorophenyl)]methyl-D,L-cysteine;
S-[α-(5,6,7,8-Tetrahydronaphth-2-yl)-α-(2-nitrophenyl)]methyl-N-methyl-D,L-cysteine;
S-[α-(5,6,7,8-Tetrahydronaphth-2-yl)-α-(3-trifluoromethylphenyl)]methyl-N-methyl-D,L-cysteine; and
S-[α-(5,6,7,8-Tetrahydronaphth-2-yl)-α-(4-cyanophenyl)]methyl-N-methyl-D,L-cysteine.

* * * * *